United States Patent
Vogt et al.

(10) Patent No.: US 10,166,057 B2
(45) Date of Patent: Jan. 1, 2019

(54) STORAGE AND MIXING SYSTEM WITH COMPRESSIBLE INTERNAL CARTRIDGE FOR PASTY STARTING COMPONENTS

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 15/490,222

(22) Filed: Apr. 18, 2017

(65) Prior Publication Data

US 2017/0311999 A1 Nov. 2, 2017

(30) Foreign Application Priority Data

Apr. 28, 2016 (DE) .......................... 10 2016 107 911

(51) Int. Cl.
*A61B 17/88* (2006.01)
*A61L 24/06* (2006.01)
(Continued)

(52) U.S. Cl.
CPC ...... *A61B 17/8833* (2013.01); *A61B 17/8822* (2013.01); *A61B 17/8825* (2013.01);
(Continued)

(58) Field of Classification Search
CPC .............. B65D 81/325; B65D 81/3233; B65D 81/3244; B65D 83/0072; B01F 5/0615;
(Continued)

(56) References Cited

U.S. PATENT DOCUMENTS 2,446,501 A 8/1948 Weber
3,188,056 A 6/1965 Trumbull et al.
(Continued)

FOREIGN PATENT DOCUMENTS

DE 202005010206 U1 9/2005
DE 102007052116 A1 4/2009
(Continued)

OTHER PUBLICATIONS

Australian Office Action for corresponding application No. 2017201631 dated May 18, 2019.
(Continued)

*Primary Examiner* — Paul R Durand
*Assistant Examiner* — Randall Gruby
(74) *Attorney, Agent, or Firm* — Norris McLaughlin P.A.

(57) ABSTRACT

Storage and mixing systems and methods for pasty multi-component polymethylmethacrylate bone cements, the systems and methods comprise a first tubular cartridge with a first cylindrical internal space containing a first starting component, a first dispensing plunger, a second tubular cartridge that is arranged within the first tubular cartridge. The external wall of the second cartridge touches against the internal wall of the first cartridge and is attached to the internal wall of the first cartridge, whereby the second cartridge contains a second starting component and has a second dispensing plunger arranged in it, whereby a pressing device with a clamping edge for compressing the second cartridge that can be propelled axially in the internal space of the first cartridge is arranged, as seen from the cartridge head, behind the first dispensing plunger and the second dispensing plunger. The pressing device can be propelled appropriately in the direction of the cartridge head such that the second cartridge is being progressively compressed axially during the motion of the pressing device such that, in
(Continued)

the process, the first dispensing plunger and the second dispensing plunger are propelled in the direction of the cartridge head.

27 Claims, 17 Drawing Sheets

(51) Int. Cl.
| | |
|---|---|
| B01F 3/08 | (2006.01) |
| B01F 3/10 | (2006.01) |
| B01F 5/06 | (2006.01) |
| B01F 13/00 | (2006.01) |
| B01F 15/00 | (2006.01) |
| B01F 15/02 | (2006.01) |
| B05C 17/005 | (2006.01) |
| C04B 26/06 | (2006.01) |
| B65D 81/32 | (2006.01) |
| A61C 5/64 | (2017.01) |
| C04B 111/00 | (2006.01) |

(52) U.S. Cl.
CPC ............... *A61C 5/64* (2017.02); *A61L 24/06* (2013.01); *B01F 3/0869* (2013.01); *B01F 3/10* (2013.01); *B01F 5/0614* (2013.01); *B01F 5/0615* (2013.01); *B01F 13/0023* (2013.01); *B01F 15/0087* (2013.01); *B01F 15/0237* (2013.01); *B05C 17/00559* (2013.01); *B05C 17/00576* (2013.01); *B05C 17/00583* (2013.01); *B05C 17/00593* (2013.01); *B65D 81/325* (2013.01); *C04B 26/06* (2013.01); *A61B 2017/8838* (2013.01); *B01F 2215/0029* (2013.01); *C04B 2111/00836* (2013.01)

(58) Field of Classification Search
CPC ............... B01F 5/0614; B01F 15/0087; B01F 15/0237; B01F 13/0023; B01F 3/0869; B01F 3/10; B05C 17/00583; B05C 17/00559; B05C 17/00576; B05C 17/00593; A61L 24/06; C04B 26/06; A61C 5/64
See application file for complete search history.

(56) References Cited

U.S. PATENT DOCUMENTS

| | | | | |
|---|---|---|---|---|
| 3,266,671 A * | 8/1966 | Gelpey | ............. | B65D 81/3233 206/219 |
| 3,323,682 A * | 6/1967 | Creighton, Jr. | ... | B05C 17/00513 222/105 |
| 3,620,417 A * | 11/1971 | Simms | ................... | B65D 35/30 222/136 |
| 4,040,420 A * | 8/1977 | Speer | ...................... | A61M 5/19 604/191 |
| 4,340,154 A * | 7/1982 | VanManen | .......... | B65D 35/242 222/136 |
| 4,366,919 A * | 1/1983 | Anderson | ......... | B05C 17/00513 222/137 |
| 4,493,436 A | 1/1985 | Brokaw | | |
| 5,050,774 A * | 9/1991 | Camm | .................. | B01F 13/002 222/137 |
| 5,443,182 A * | 8/1995 | Tanaka | .................. | B01F 13/002 222/129 |
| 5,566,860 A * | 10/1996 | Schiltz | ............. | B05C 17/00513 222/105 |
| 5,647,510 A * | 7/1997 | Keller | ............... | B05C 17/00513 222/94 |
| 5,918,772 A * | 7/1999 | Keller | ............... | B05C 17/00506 222/145.5 |
| 6,454,129 B1 | 9/2002 | Green | | |
| 6,634,524 B1 * | 10/2003 | Helmenstein | ..... | B05C 17/00553 222/105 |
| 6,681,957 B1 * | 1/2004 | Green | ............... | B05C 17/00553 222/135 |
| 6,769,574 B1 * | 8/2004 | Keller | ............... | B05C 17/00509 222/137 |
| 6,935,541 B1 | 8/2005 | Campbell et al. | | |
| 6,938,797 B2 | 9/2005 | Brugner et al. | | |
| 7,237,693 B2 * | 7/2007 | Brennan | ........... | B05C 17/00506 222/137 |
| 7,793,800 B2 | 9/2010 | Griesbaum et al. | | |
| 7,874,458 B2 * | 1/2011 | Sogaro | ............. | B05C 17/00506 222/137 |
| 8,197,545 B2 * | 6/2012 | O'Neil | .................. | A61F 2/4611 623/17.12 |
| 8,544,683 B2 | 10/2013 | Springhorn et al. | | |
| 9,227,218 B1 | 1/2016 | Lin | | |
| 9,517,488 B2 * | 12/2016 | Frey | .................. | B05C 17/00516 |
| 9,901,946 B2 * | 2/2018 | Ettlin | ...................... | B05C 17/01 |
| 2004/0074927 A1 | 4/2004 | Lafond | | |
| 2004/0129122 A1 | 7/2004 | Brugner et al. | | |
| 2006/0151531 A1 * | 7/2006 | Tikusis | ................ | B01F 5/0603 222/145.6 |
| 2007/0017931 A1 * | 1/2007 | Sogaro | ................ | B65D 41/485 222/137 |
| 2008/0206712 A1 * | 8/2008 | Kennard | .................. | A61C 3/16 433/180 |
| 2009/0105144 A1 | 4/2009 | Vogt et al. | | |
| 2009/0105366 A1 | 4/2009 | Vogt et al. | | |
| 2009/0314803 A1 * | 12/2009 | Keller | ................. | B01F 11/0082 222/136 |
| 2014/0008391 A1 * | 1/2014 | Lin | ...................... | B65D 81/325 222/136 |
| 2015/0284166 A1 * | 10/2015 | Green | ..................... | B05C 11/10 222/1 |

FOREIGN PATENT DOCUMENTS

| | | |
|---|---|---|
| DE | 102007050762 B3 | 5/2009 |
| DE | 102008030312 A1 | 1/2010 |
| DE | 202014102416 U1 | 7/2014 |
| EP | 1392450 B1 | 7/2005 |
| EP | 2 862 812 A1 | 4/2015 |
| FR | 1468507 A | 2/1967 |
| WO | 2005/016783 A1 | 2/2005 |

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.
German Office Action from corresponding German Patent Application No. DE10 2016 107 911.1 dated Nov. 18, 2016.

* cited by examiner

STORAGE AND MIXING SYSTEM WITH COMPRESSIBLE INTERNAL CARTRIDGE FOR PASTY STARTING COMPONENTS

This application claims foreign priority benefit under 35 U.S.C. 119 of German Application No. DE 10 2016 107 911.1 filed Apr. 28, 2016.

DESCRIPTION OF DISCLOSURE

The invention relates to a storage and mixing system for pasty multicomponent polymethylmethacrylate bone cements, whereby the storage and mixing system comprises a first tubular cartridge having an internal space.

The invention also relates to a method for mixing pasty starting components of a bone cement, in particular of a pasty multicomponent polymethylmethacrylate bone cement using said storage and mixing system.

Accordingly, the subject matter of the invention is a simple, inexpensively produced storage and mixing system for pasty multicomponent polymethylmethacrylate bone cements by means of which high viscosity pasty starting components of the polymethylmethacrylate bone cement can be mixed and dispensed even with manually operated extrusion devices.

Conventional polymethylmethacrylate bone cements (PMMA bone cements) are made from a powdered component and a liquid monomer component (K.-D. Kühn: Knochenzemente für die Endoprothetik: Ein aktueller Vergleich der physikalischen and chemischen Eigenschaften handelsüblicher PMMA-Zemente. Springer-Verlag Berlin Heidelberg New York, 2001). After mixing the cement powder with the liquid monomer component, said polymethylmethacrylate bone cements are applied in their non-cured pasty state in the form of a cement dough. If mixing systems are used with powder-liquid cements, the cement dough is situated in a cartridge. The cement dough is squeezed from said cartridge through the motion of a dispensing plunger. The dispensing plungers usually have a diameter of between 30 mm and 40 mm and thus have a surface area of 7.0 cm² to 12.5 cm² on the outside that is engaged by the pestle of the extrusion device during the extrusion process. The motion of the dispensing plunger is effected by manually operated mechanical extrusion devices, which are also called applicators. Said extrusion devices, or applicators, usually have an extrusion force in the range of approximately 1.5 kN to 3.5 kN.

Pasty two-component bone cements, such as are known, e.g., from DE 10 2007 050 762 B3, DE 10 2008 030 312 A1, and DE 10 2007 052 116 B4, are a recent development. In these two-component bone cements, two pasty components are stored in two separate cartridges with two separate dispensing plungers. During application, both pastes are pressed from the interior spaces of the cartridges into a static mixer through the motion of the dispensing plungers, and are dispensed through a dispensing tube once the mixing took place. If the composition of the pasty starting components is appropriate, a tack-free cement dough that is ready for application is obtained after the two starting components are mixed. Accordingly, there are none of the waiting times until the cement dough becomes tack-free which were always obligatory with the previous conventional polymethylmethacrylate bone cements. This allows valuable OR time to be saved.

The application of the previous conventional PMMA bone cements, which consist of a liquid monomer component and a separately stored cement powder component as starting components, involves the two starting components being mixed in cementing systems and/or vacuum cementing systems and the cement dough thus formed then being extruded by means of manually operated extrusion devices. These simple mechanical extrusion devices utilise, in particular, clamp rods that are driven by a manually-actuated tilting lever for extrusion. The manually driven extrusion devices are time-proven throughout the world for decades and as such are the current prior art. Said extrusion devices are advantageous in that the medical user has a feel for the penetration resistance of the bone cement dough into the bone structures (cancellous bone) by means of the manual force to be expended.

In the case of high viscosity pasty starting components and the use of cartridges, in which the dispensing plungers have a total surface area in the range of 7.0 cm² to 12.5 cm² at the external plunger sides, which are engaged by the pestles of the extrusion devices, these devices can be operated manually either not at all or only while expending a very large force. This exertion of a large force is unreasonable for medical users in the OR.

From the adhesives and sealant industry, electrically driven extrusion devices are known as well. Said devices can be driven both with rechargeable batteries and batteries or by means of a stationary electrical power supply. Said devices can extrude particularly thick pasty masses since their extrusion force is very large in some cases. However, it is one disadvantage of the use of electrical motors that these motors contain non-ferrous metals and are expensive purchases. Since the OR area needs to be kept sterile, said devices need to be sterilised with much effort or even replaced. The presence of electrical wiring may impede the mobility of the user in the OR.

Moreover, pneumatic devices have been proposed as well. Said devices require a stationary or mobile compressed air connection (U.S. Pat. No. 2,446,501 A; DE 20 2005 010 206 U1). This necessitates compressed air hoses, which may impede the mobility of the user.

Alternatively, the use of compressed gas cartridges to provide compressed gas is feasible just as well. Devices have been proposed for this purpose, in which the supply of compressed gas is controlled by a valve and, in addition, the flow of the viscous mass is controlled by a second valve (US 2004/0074927 A1; U.S. Pat. No. 6,935,541 B1). In these devices, the gas cartridges are integrated into the devices. These systems, which are connected to compressed air or contain compressed gas cartridges, always necessitate the presence of a compressed gas source in the absence of which the systems cannot be used.

U.S. Pat. No. 8,544,683 B2 discloses a cartridge system that is suitable for admixing a small amount to a main starting component. The cartridge system has, aside from a cartridge, a second smaller cartridge arranged in it, whereby, along with the propulsion of a dispensing plunger in the larger cartridge, a dispensing plunger in the smaller cartridge is also driven by a joint connecting element. However, the system is not suitable for mixing the very viscous pasty starting components of PMMA bone cement.

A coaxial cartridge system containing a special plunger system is described in the patent, EP1 392 450 B1. In construction materials chemistry, a cartridge system is used for storing and mixing pasty two-component sealant masses. The plunger system disclosed therein has a cylindrical dispensing plunger for the central cartridge and a ring-shaped dispensing plunger for the second, coaxially arranged cartridge. Both dispensing plungers are driven downstream from the sealant surfaces by means of a support element that possesses, on its rear side, multiple support surfaces for the pestle of the extrusion device. The support element contains arc-shaped blades. Upon the axial action of a pestle of an extrusion device, both dispensing plungers are moved forward in the direction of the cartridge head. In the process, the pasty components contained in the coaxial cartridges are pushed in the direction of the cartridge head. Simultaneously, the two blades cut the wall of the internal coaxial cartridges into two parts. This system is disadvantageous in that it is inevitable that two cutting processes proceed simultaneously. This means, that energy needs to be expended for both cutting processes, which is then not available for the actual propulsion of the two pasty components. Due to the static mixers being arranged in the dispensing tube and the viscosity of the starting components being high, the mixing of pasty starting components for PMMA bone cements requires a very large amount of propulsion energy that cannot be provided manually, without a hazard and with conventional extrusion devices in the case of larger-sized cartridges. Therefore, a loss of propulsion energy due to two cutting processes proceeding in tandem can be problematic, especially in the case of highly viscous pasty components. Moreover, coaxial cartridges are not easy to fill with the viscous pasty main starting component of a PMMA bone cement. Especially if only small amounts of the PMMA bone cement are to be contained therein, the free cross-sections of the external coaxial cartridge for the main starting component become so small that they cannot be filled using conventional procedures.

Patent FR 1 468 507 discloses a cartridge system, in which a tubular storage container is arranged in a cartridge. That latter is connected in one place to the cartridge on the end of the cartridge. The cartridge has arranged in it a dispensing plunger, which possesses an opening, in which a part of the tubular storage container is arranged, whereby the opening is smaller than the diameter of the tubular storage container. During the forward motion of the dispensing plunger in the direction of the cartridge head, the mass contained in the cartridge is extruded and the mass contained in the tubular container is moved in the direction of the cartridge head by squeezing-out. For the function of squeezing-out, it is important that the tubular storage container is affixed on the end of the cartridge such that the tubular storage container does not move forward in the direction of the cartridge head along with the dispensing plunger during the squeezing-out without the mass contained therein being extruded. It is a disadvantage of the proposed system that necessarily smaller or larger amounts of the mass to be extruded remain in the tubular storage container due to the simple squeezing-out on an opening. The tube creases uncontrollably and unpredictably during the squeezing out and remainders of the material to be squeezed out stay behind in these creases. As a result, the use of this storage system with multicomponent bone cement pastes is not feasible or only conditionally, since the contents of the at least two initiator components that are arranged separately in the first starting component and in the second starting component have to be exactly defined for the curing of the bone cement to be reproducible. Accordingly, any variation of the mixing ratio needs to be prevented as much as possible. Moreover, due to the chemical composition of the starting components, the cartridges with remainders of the starting components need to be discarded with great effort.

Accordingly, it is the object of the invention to overcome the disadvantages of the prior art. Specifically, a simple, inexpensive-to manufacture storage and mixing system for pasty multicomponent polymethylmethacrylate bone cements and a method for producing a cement dough using a storage and mixing system are to be provided, whereby it shall be feasible to ready the storage and mixing system for use as a single-use, ready-to-use system in simplest manner with a minimal number of assembly steps within a few seconds and whereby the storage and mixing system, following connection to manually drivable medical extrusion devices and/or applicators, generates a homogeneously mixed cement dough and dispenses it at the dispensing opening of a dispensing tube right after the start of manual actuation of the extrusion device. It shall be feasible to utilise the manually operated extrusion devices used thus far in ORs for the conventional polymethylmethacrylate bone cements, possessing one push rod each and/or one pestle each and, if applicable, one plunger cup each, for dispensation of the two-component polymethylmethacrylate bone cement and/or of the cement dough by means of the storage and mixing system to be developed. By this means, the purchase of special extrusion devices for dispensation of pasty two-component polymethylmethacrylate bone cements is to be avoided.

Preferably, the storage and mixing system to be developed shall necessitate no push rods and/or pestles that are connected to each other and are propelled synchronously in order for the entire device not to become significantly longer and larger than the mixing systems and vacuum mixing systems that are thus far customary for the conventional powder-liquid polymethylmethacrylate bone cements. Presently, a simple solution is to be found that allows, if at all possible with just one push rod and/or just one pestle and, if applicable, one plunger connected thereto, the propulsion of two or more pasty starting components from the device both synchronously and manually. It shall be feasible to safely store the pasty starting components of the bone cement separately from each other within the storage and mixing system. For application, it shall be feasible to safely combine both pasty starting components.

It shall also be feasible to extrude all of the two starting components from the cartridges such that the mixing ratio of the initiator components can be reproduced in order to provide for reproducible processing properties of the mixed cement dough and mechanical properties of the cured cement.

The storage and mixing system shall also allow a small volume of the homogeneously mixed cement dough of approximately 40 mL and/or maximally 70 mL to be dispensed without any substantial residual amounts (more than 15 mL) remaining in the system and needing be discarded with great effort. More substantial volumes of the cement dough are not desired for preferred applications. This is because the specified low amounts are sufficient for many such applications, such as operations (OPs) on the knee.

The storage and mixing device shall allow for storage and extrusion of two pastes at a volume ratio of more than or equal to 95 to 5 or preferably more than or equal to 98 to 2. In this context, the device is intended for those pasty multicomponent polymethylmethacrylate bone cements, in which a low-volume pasty starting component can be mixed very easily with a large-volume pasty starting component, whereby the low-volume pasty starting component dissolves within a few seconds in the large-volume pasty starting component.

The transition from the cartridge to the dispensing tube shall be designed appropriately such that the flow resistance of the pasty starting components during the extrusion is as low as possible. Preferably, pasty starting components that can be applied right after the extrusion, i.e. where there is no time required for swelling of the PMMA bone cement, are used as starting components. The device shall be designed appropriately such that mistaking the relevant assembly steps by the user is excluded to the extent possible by design means and such that the storage and mixing system can be implemented by largely untrained personnel as well. Moreover, a method for mixing the pasty starting components and for dispensing the homogeneously mixed cement dough shall be provided.

The objects of the invention are met by a storage and mixing system for pasty multicomponent polymethylmethacrylate bone cement, whereby the storage and mixing system comprises a) a first tubular cartridge with a first cylindrical internal space, whereby a first starting component of a multicomponent bone cement is contained in the internal space;

b) a first dispensing plunger that is arranged in the first internal space of the first cartridge such as to be axially mobile and that is provided for expelling the first starting component from the first cartridge through an opening in the cartridge head of the first cartridge that is opposite from the first dispensing plunger;

c) a second tubular cartridge that is arranged within the first tubular cartridge, whereby the external wall of the second cartridge touches against the internal wall of the first cartridge and is attached to the internal wall of the first cartridge, whereby the second cartridge contains a second starting component of the multicomponent bone cement and has a second dispensing plunger arranged in it, whereby the second dispensing plunger can be used to expel the second starting component from the second cartridge through an opposite opening in the second cartridge in the region of the cartridge head of the first cartridge;

d) whereby a pressing device with a clamping edge for compressing the second cartridge that can be propelled axially in the internal space of the first cartridge is arranged, as seen from the cartridge head, behind the first dispensing plunger and the second dispensing plunger, whereby the pressing device can be propelled appropriately in the direction of the cartridge head such that the second cartridge is being progressively compressed axially during the motion of the pressing device such that, in the process, the first dispensing plunger and the second dispensing plunger are propelled in the direction of the cartridge head.

Preferably, the internal space of the first (external) cartridge has a cylindrical geometry. The same applies to the internal space of the second (internal) cartridge prior to the deformation of the wall of the second cartridge. The cylindrical shape is the simplest shape by means of which the internal spaces of the cartridges can be implemented. A cylindrical space shall be understood geometrically to mean the shape of a general cylinder with any footprint, i.e. not just a cylinder with a circular footprint. Accordingly, the limiting internal wall of the internal space can be a cylinder with any footprint and the jacket can be a cylinder with any footprint, i.e. including a non-circular or circular footprint. However, according to the invention, a cylindrical geometry with a rotationally symmetrical and, in particular, circular footprint is preferred for the internal space of the first cartridge, since the same is the easiest to manufacture. The wall of the second cartridge can be attached appropriately to the internal wall of the first cartridge such that a cylindrical symmetry of the second internal space deviates from the circular footprint.

The pressing device and the first dispensing plunger can just as well be provided to be one-part or firmly connected to each other.

The starting components of the multicomponent bone cement, in particular of the multicomponent polymethylmethacrylate bone cement, are preferred to be fluid, particularly preferably are pasty.

The first dispensing plunger preferably closes tight against the internal wall of the first cylindrical internal space and the second dispensing plunger closes tightly against the internal wall of the second cylindrical internal space. In this context, the second cylindrical internal space is not deformed. Particularly preferably, the first dispensing plunger closes tightly against the external wall of the second cartridge in the area, in which the external wall of the second cartridge limits the internal wall of the first cartridge.

The present invention proposes to have the external wall of the second cartridge be attached to the internal wall of the first cartridge, in the front in the area of the cartridge head and in the back behind the second dispensing plunger, whereby the external wall of the second cartridge preferably is attached to the internal wall of the first cartridge along the entire length of the second cartridge.

This prevents the second cartridge from moving uncontrolled within the first cartridge and ensuing leakage of the second cartridge, which is being deformed, from arising. A connection and/or attachment of the second cartridge along the entire length of the second cartridge is particularly well-suited for this purpose. Moreover, this can be manufactured easily as well.

The invention can provide the openings to be closed by a detachable closure, in particular by detachable stoppers on the cartridge head.

By this means, the internal spaces of the storage and mixing system are closed off with respect to the outside, on the sides by the cylindrical internal spaces, on the rear by the dispensing plunger, and on the front by the detachable closures. By this means, the storage and mixing system is suitable for long-term storage of the starting components.

The invention can just as well provide the first dispensing plunger and the second dispensing plunger to be propelled parallel with respect to each other during the propulsion of the pressing device, preferably the first dispensing plunger and the second dispensing plunger run at the same level in the direction of the cartridge head.

By this means, uniform mixing of the starting components is attained, whereby the mixing ratio and thus the properties of the bone cement to be mixed is/are consistent.

Moreover, the invention can provide an attachment means, in particular an external thread, on the outside of the first cartridge in the region of the cartridge head.

By this means, on the one hand, a closure for closing the openings of the cartridges can be attached to the first cartridge and, on the other hand, a dispensing tube and a static mixer can be attached on the front of the openings. These need to comprise a matching counter-attachment means, preferably a matching internal thread.

The invention can provide preferred storage and mixing systems to comprise a dispensing tube with a static mixer that can be attached to the first cartridge, preferably can be attached to the attachment means on the first cartridge, whereby it is particularly preferred to provide on the dispensing tube an internal thread matching the external thread on the first cartridge and/or to provide elements of a bayonet closure and/or snap-in elements of a snap-in closure.

This completes the storage and mixing system even further. The storage and mixing system is then also well-suited for application of the mixed bone cement. Having the static mixer attains stronger mixing of the starting components and a more homogeneous bone cement dough is generated.

In this context, the invention can provide the ratio of the internal diameter of the first cartridge and the internal diameter of the dispensing tube to be less than 5 to 2, whereby the ratio of the internal diameter of the first cartridge and the internal diameter of the dispensing tube preferably is less than or equal to 2 to 1, and particularly preferably the ratio of the internal diameter of the first cartridge and the internal diameter of the dispensing tube is 8 to 5.

As a result, a sufficient flow rate of the bone cement is generated at the dispensing opening of the dispensing tube when the dispensing plunger is propelled.

The invention can just as well provide the internal diameter of the first cartridge to be at most 25 mm and the internal diameter of the dispensing tube to be at most 15 mm, whereby, preferably, the internal diameter of the cartridge is at most 20 mm and the internal diameter of the dispensing tube is at most 12 mm.

Due to the inventive design of the cartridges and/or of the cartridges and the dispensing tube, it is feasible to accommodate the often particularly viscous and pasty starting components of the bone cement, in particular with regard to the first starting component, in a single cartridge which, in addition, can still be extruded by action of a manual force and which can still be filled using conventional techniques. When the diameters are larger, the action of a manual force is not sufficient or not sufficient without further ado for extruding the viscous pasty starting components of the bone cement from the cartridge. Accordingly, with the diameters as specified, the advantages of the present invention are particularly evident.

Moreover, the invention can provide the ratio of the internal diameter of the first cartridge and the distance between the first dispensing plunger in the cartridge head to be at most 1 to 10, whereby, preferably, the ratio of the internal diameter of the first cartridge and the distance between the first dispensing plunger and the cartridge head is at most 1 to 15.

This ensures that the deformation of the second cartridge does not impede the motion of the pressing device too strongly such that the storage and mixing system can still be driven by the action of a reasonable manual force.

Preferred storage and mixing systems can also be characterized in that the clamping edge is inclined with respect to the longitudinal axis of the first cartridge, and preferably is inclined at an angle of at least 40° with respect to the longitudinal axis of the first cartridge, particularly preferably is inclined at an angle between 40° and 80° with respect to the longitudinal axis of the first cartridge.

As a result, the wall of the second cartridge is deformed over a larger inclined surface area, which simplifies the propulsion and allows the deformation to proceed more uniformly. Concurrently, the deformation is sufficient to uniformly drive the second dispensing plunger on the backside by means of the deforming wall of the second cartridge.

The invention also proposes to have the clamping edge squeeze the second cartridge and/or the wall of the second cartridge against the internal wall of the first cartridge when the pressing device is being propelled.

As a result, the wall of the cartridge is pushed as far as possible from the range of action of a following pestle of an extrusion device such that the same cannot impede the motion thereof.

Moreover, the invention can provide the clamping edge to cover at least 30% of the surface area of the cross-section of the second cartridge, preferably covers at least 60% of the surface area of the cross-section of the second cartridge.

This attains a sufficient deformation such that the second dispensing plunger can be driven by the deforming wall of the second cartridge. Moreover, the wall of the cartridge is also pushed efficiently far from the range of action of a following pestle of an extrusion device such that the same cannot impede the motion thereof.

Preferably, the invention provides a gap between the pressing device and the internal wall of the first cartridge in the region of the second cartridge, whereby the gap is as wide as or wider than the thickness of the wall of the second cartridge.

As a result, the pressing device can run over the deformed second cartridge without the material of the wall of the second cartridge as such having to be compressed and without a deformation of the first cartridge being required, which would lead to an undesired additional expenditure of force during the propulsion of the pressing device.

The invention further proposes the rear side of the pressing device to be designed as a support surface for a pestle of an extrusion device.

By this means, the pressing device can be driven easily using a conventional extrusion device.

According to a preferred refinement, the invention proposes the diameter of the internal space of the first cartridge to be smaller than or equal to 25 mm, whereby the diameter of the internal space of the first cartridge preferably is smaller than or equal to 20 mm, and/or the first cartridge to have an internal diameter of at most 25 mm and the second cartridge to have an internal diameter of at most 5 mm, preferably the first cartridge to have an internal diameter of at most 20 mm and the second cartridge to have an internal diameter of at most 3 mm.

Due to the inventive design of the first cartridges and/or of the first and second cartridge, it is feasible to accommodate the often particularly viscous and pasty starting components of the bone cement, in particular with regard to the first starting component, in a single storage and mixing system, which can still be extruded by action of a manual force and which can still be filled using conventional techniques. When the diameters are larger, the action of a manual force is not sufficient or not sufficient without further ado for extruding the viscous pasty starting components of the bone cement from the cartridge and/or cartridges. Accordingly, with the diameters as specified, the advantages of the present invention are particularly evident.

The invention can also provide the clamping edge, by squeezing the second cartridge, to press the thus deformed wall of the second cartridge against the underside of the second dispensing plunger and to thus push the second dispensing plunger in the direction of the cartridge head while the pressing device is being propelled in the direction of the cartridge head.

As a result, a separate or complex drive for the second dispensing plunger can be foregone. Without the second dispensing plunger, simple squeezing-out of the second starting component from the deforming second cartridge would lead to undesired variations in the composition of the bone cement, since the deformation of the second cartridge is associated with the formation of creases, in which unpredictable residual amounts of the second starting components remain and are not being mixed with the first starting component. In contrast, the propulsion of the second dispensing plunger, which can be sealed against the internal wall of the second cartridge by means of seals and/or wiper lips, is always associated with the entire content of the second cartridge being conveyed and expelled.

Preferred embodiments of the invention can be characterised in that the first cartridge, the second cartridge, the cartridge head, and the dispensing plungers are made from plastic material, whereby polyethylene-co-vinylalcohol (EVOH), polybutylene-terephthalate (PBT), polyethylene-terephthalate (PET), and polymethacryl acid methylester-co-acrylonitrile are preferred as plastic materials.

The design with plastic materials is inexpensive and easy to implement. The preferred plastic materials are particularly well-suited due to their resistance with respect to the chemicals contained in the starting components.

The present invention proposes the pressing device or the clamping edge to be manufactured from metal and/or plastic material and/or glass fibre-reinforced plastic material, whereby the pressing device or the clamping edge is manufactured from steel, aluminium alloys, zinc alloys, polyamide, glass fibre-reinforced polyamide, polyetherketone, polysulfone or combinations of said materials.

Due to the hardness of said materials, a sufficient deformation of the second cartridge can be attained without the clamping edge itself being deformed too strongly.

Preferred storage and mixing systems can just as well be characterised in that the ratio of the volume of the first cartridge and the volume of the second cartridge is at least 95 to 5, preferably is at least 98 to 2.

By this means, small and/or low amounts of a second component are admixed and thus the advantages of the design according to the invention are utilised particularly well. This is the case, because the storage and mixing system according to the invention is characterised in that even such extreme mixing ratios can still be generated homogeneously.

Moreover, the invention can provide the second cartridge to be squeezed appropriately, when the pressing device is exposed to at least 0.5 kN acting in the direction of the cartridge head, such that the squeezed second cartridge fits through a gap between the clamping edge and the internal wall of the first cartridge.

Preferably, this is attained through the selection of a suitable thickness of the wall of the second cartridge and through the selection of a suitable material for the second cartridge. What this attains is that the storage and mixing system can be extruded and/or used with the expenditure of a manual force.

Moreover, the invention can provide the ratio of the thickness of the wall of the first cartridge and the thickness of the wall of the second cartridge to be at least 11 to 10, and whereby the ratio of the thickness of the wall of the first cartridge and the thickness of the wall of the second cartridge is at least 2 to 1, particularly preferably is at least 3 to 1.

This applies in case the first and the second cartridge are made from the same material. If the internal second cartridge consists of the material with a lower modulus of elasticity and/or a more easily deformed material, the wall thickness of the second internal cartridge can also be selected to be equal to or even larger than the wall thickness of the external cartridge. By this means, the internal second cartridge can be deformed without the external first cartridge being deformed along with it and thus inhibiting the motion of the pressing device and of the dispensing plungers.

The internal second cartridge can be welded into the first cartridge in the form of a finished part. This is important, in particular, if the two cartridges do not consist of the same material.

A refinement of the present invention proposes a part of the wall of the first cartridge to form a part of the internal wall of the second cartridge, preferably over the entire length of the second cartridge or over at least 80% of the entire length of the second cartridge, and/or a part of the wall of the first cartridge to limit a part of the second internal space of the second cartridge, preferably over the entire length of the second cartridge or over at least 80% of the entire length of the second cartridge.

By this means, a motion of the second cartridge with respect to the first cartridge is restricted particularly effectively. Moreover, the deformation of the wall of the second cartridge can be pre-defined particularly well by this means.

The invention can provide the thickness of the wall of the first cartridge to be at least 1 mm and the [thickness of] the wall of the second cartridge to be at most 0.5 mm.

By this means only the second cartridge is subject to plastic deformation, whereas the first cartridge is not subject to plastic deformation.

The invention can provide the second cartridge to be plastically deformed and/or plastically deformable by the clamping edge.

Moreover, the invention can provide the first cartridge to comprise, on the exterior on the wall on the side opposite from the cartridge head, an attachment means by means of which the storage and mixing system can be connected to an extrusion device.

Moreover, the invention can provide the cartridge head to be designed to have a rubber-elastic plate and a union cap or union nut made of plastic material, whereby the union cap or union nut blocks the rubber-elastic plate by means of a protruding edge, and whereby at least the two openings of the first and second cartridges are arranged in the rubber-elastic plate and are closed by means of a stopper.

In this context, the invention can provide the union cap or union nut to comprise, as connecting element, an internal thread or an external thread or a bayonet closure or snap-in elements for a snap-in closure to the first cartridge.

Moreover, the invention can provide a plastic plate with two openings, which can be or are closed by stoppers, to be arranged in the cartridge head on or under the rubber elastic plate.

Moreover, the invention can preferably provide the front face of the cartridge to be designed as the cartridge head, whereby at least two openings, which can be closed by stoppers, penetrate through the front face of the cartridge. The closable openings preferably form the two openings of the first cartridge and of the second cartridge.

Preferably, the invention can just as well provide at least 40% of the front face of the cartridge to be closed by a plate, whereby the opening of the second cartridge is arranged in the non-closed part of the front face. By this means, the mixing of the small-volume second starting component with the large-volume first starting component is promoted.

The invention can just as well provide a third tubular cartridge to be arranged inside the first tubular cartridge, whereby the external wall of the third cartridge touches against the internal wall of the first cartridge and is attached to the internal wall of the first cartridge, whereby the third cartridge contains the second starting component or a third starting component of the multicomponent bone cement and has a third dispensing plunger arranged in it, whereby the second starting component or the third starting component can be expelled from the third cartridge, by means of the third dispensing plunger, through an opposite opening in the third cartridge in the region of the cartridge head of the first cartridge, whereby the pressing device is arranged behind the third dispensing plunger as seen from the cartridge head and the pressing device comprises a clamping edge for compressing the third cartridge, whereby the pressing device can be propelled appropriately in the direction of the cartridge head such that the third cartridge is continuously compressed axially while the pressing device moves and thus the first dispensing plunger, the second dispensing plunger, and the third dispensing plunger are being propelled in the direction of the cartridge head.

By this means, a further starting component can be mixed into the bone cement dough. The third cartridge being filled with the second starting component is advantageous in that this allows the second starting component to be admixed at different places of the first starting component and in a more homogeneous mixing of the starting components thus being attainable.

Preferably, the third tubular cartridge is arranged on the internal wall of the first cartridge that is opposite from the second cartridge. What this symmetry attains is that the action of the force acts symmetrically on the pressing device due to the deformation of the second and third cartridges. By this means, a more uniform propulsion can be attained. In particular, the risk of the pressing device becoming lodged in the first cartridge is reduced, which reduces at least the requisite force for driving the storage and mixing system, attains a more uniform dispensation of the mixed bone cement dough, and reduces or eliminates the risk of complete blockage of the storage and mixing system.

In this context, the invention can provide the third cartridge and/or the third dispensing plunger to comprise the same features as the second cartridge and/or the second dispensing plunger according to any one of the preceding storage and mixing systems.

This applies in particular, with respect to the interaction of the third cartridge and/or of the third dispensing plunger with other components of storage and mixing systems according to the invention. This results in the same advantages as with the second cartridge and/or the second dispensing plunger.

The invention can just as well provide at least one fourth tubular cartridge to be arranged inside the first tubular cartridge, whereby the external wall of the at least one fourth cartridge touches against the internal wall of the first cartridge and is attached to the internal wall of the first cartridge, whereby the at least one fourth cartridge contains the second, the third, a fourth and/or each at least one further starting component of the bone cement and the at least one fourth cartridge has a fourth dispensing plunger each arranged in it, whereby the second, the third, the fourth and/or the respective further starting component can be expelled from the at least one fourth cartridge, by means of the fourth dispensing plunger, through an opposite opening in the at least one fourth cartridge in the region of the cartridge head of the first cartridge, whereby the pressing device is arranged behind the fourth dispensing plunger or plungers, as seen from the cartridge head, and the pressing device comprises at least one clamping edge for compressing the at least one fourth cartridge, whereby the pressing device can be propelled appropriately in the direction of the cartridge head such that the at least one fourth cartridge is continuously compressed axially while the pressing device moves and thus the first dispensing plunger, the second dispensing plunger, the third dispensing plunger, and the fourth dispensing plunger or plungers are being propelled in the direction of the cartridge head.

Again, the invention can preferably provide that the at least one fourth cartridge and/or the respective fourth dispensing plunger where plungers comprise the same features as the second cartridge and/or the second dispensing plunger of storage and mixing systems according to the invention.

This applies, in particular, with respect to the interaction of the at least one fourth cartridge and/or of the fourth dispensing plunger or respected fourth dispensing plungers with other components of storage and mixing systems according to the invention. The invention can just as well provide the at least one fourth cartridge together with the second and third cartridges to be arranged symmetrically with respect to the axis of the first cartridge in order to attain uniform mixing of all starting components and a uniform action of force on the cartridges and on the pressing device.

The objects underlying the present invention are also met by a method for the mixing of starting components of a pasty cement dough, in particular of a pasty multicomponent polymethylmethacrylate bone cement dough, with a storage and mixing system according to the invention, comprising the following steps proceeding in the order given:

a) Removing the cartridge head from the first cartridge or opening the openings of the first cartridge and of the second cartridge;

b) attaching and connecting a dispensing tube to the front side of the first cartridge;

c) inserting the first cartridge into an extrusion device, whereby the extrusion device comprises a pestle that can be propelled axially for propelling the pressing device on the interior of the first cartridge in the direction of the dispensing tube;

d) extruding the starting components by means of the extrusion device by axially propelling the pestle, whereby the pressing device is propelled in the direction of the dispensing tube by the pestle, the first dispensing plunger is pushed in the direction of the dispensing tube by the pressing device, the clamping edge of the pressing device presses the wall of the second cartridge to the internal wall of the first cartridge, the deformed wall of the second cartridge pushes the second dispensing plunger in the second cartridge in the direction of the dispensing tube, whereby the starting components of the cement dough of both cartridges are being pushed into the dispensing tube, whereby the starting components are mixed in the dispensing tube to form the pasty cement dough and the mixed cement dough flows out from a dispensing opening of the dispensing tube.

In this context, the invention can provide the third cartridge in step a) to be opened according to any one of the preferred embodiments specified above, and preferably the at least one fourth cartridge to also be opened, and during propulsion of the pressing device with a pestle in the direction of the dispensing tube in step d), the clamping edge or a further clamping edge of the pressing device to press the wall of the third cartridge to the internal wall of the first cartridge, the deformed wall of the third cartridge to push the third dispensing plunger in the third cartridge in the direction of the dispensing tube and, preferably, during propulsion of the pressing device with a pestle in the direction of the dispensing tube, the clamping edge or one or more further clamping edge(s) of the pressing device to also press the respective wall of the at least one fourth cartridge to the internal wall of the first cartridge, the deformed wall or the deformed walls of the at least one fourth cartridge to push the respective fourth dispensing plunger in the at least one fourth cartridge in the direction of the dispensing tube.

By this means, multiple starting components can be mixed into a cement dough or a more symmetrical action of force can act on the pressing device such that the pressing device can lodge or be impeded less easily.

Moreover, the invention can provide the extrusion device to be driven manually, by compressed air or by a motor, whereby the manual force, the compressed air or the motor propels the pestle in the direction of the dispensing tube.

Manually drivable extrusion devices are preferred according to the invention, since they do not need to be connected to a source of compressed air or an energy source and do not need to contain this kind of source.

The invention can provide the pestle of the extrusion device to push onto the side of the pressing device facing away from the dispensing plunger, and the dispensing plungers to be driven by the pressing device.

The invention is based on finding, surprisingly, that arranging at least one internal second cartridge in a larger external first cartridge, whereby the internal second cartridge [comprises] a pressing device that runs within the external first cartridge and, in the process, propels the dispensing plungers in the cartridges and compresses the wall of the internal second cartridge and thus pushes it out of the way of the pestle of the extrusion device, allows a storage and mixing device for a multicomponent bone cement to be provided by means of which even a very small amount of at least one second starting component can be mixed at the desired mixing ratio with a first main starting component in homogeneous and reproducible manner. In this context, the storage and mixing system is also suitable for storage of the starting components and, moreover, can be manufactured inexpensively. Despite the inexpensive design, the storage and mixing device is easy to use and can also be used with manually driven extrusion devices. Moreover, the risk of blockage of the device is low such that a device that is particularly reliable in operation is being provided. The storage and mixing device can be manufactured from inexpensive materials. The dimensions of the storage and mixing device according to the invention can be designed, in this context and by this means, such as to include such small parts that even upon use of the particularly viscous starting components and/or the particularly viscous main starting component manual extrusion and mixing is still feasible. Propulsion of the viscous starting components by a static mixer requires the application of significant forces.

Moreover, it has been evident, surprisingly, that by this means a narrow cartridge with just one pressing device as the drive for propelling the dispensing plungers for propulsion of the two starting components can be used by means of which the wall or walls of the at least one internal cartridge can be cut open and pushed to the side at the same time. By this means, the force required for mixing and expelling the starting components can be minimised such that an extrusion device that can be driven by manual force can be used in conjunction with the storage and mixing system in order to expel the starting components from the cartridges and mix them with each other.

The underlying rationale of the invention is to provide, in a tubular external first cartridge, at least one second smaller internal cartridge that has a smaller cross-section than the larger external first cartridge, whereby an axially mobile dispensing plunger each is arranged in both cartridges, and to connect the larger dispensing plunger to a pressing device that pushes, by means of a clamping edge, the wall of the at least one smaller internal second cartridge against the wall of the larger first cartridge when the clamping body is moved in the direction of the cartridge head such that the cartridge wall is being deformed and such that the dispensing plunger of the smaller second cartridge is moved by the deformed wall and/or by the ongoing deformation of the wall in the direction of the cartridge head, when the pressing device is being moved forward. Concurrently, the dispensing plunger of the larger first cartridge is also moved in the direction of the cartridge head during the forward motion. The deformed, squeezed cartridge wall of the internal second cartridge slides through an external lateral opening of the pressing device during the forward motion of the pressing device. During dispensation of the pasty second starting component from the smaller second cartridge by forward motion of the second dispensing plunger, there basically remain no residual amounts of the pasty second starting component in the deformed small second cartridge. It is important in this context that the pressing device possesses, on its rear side, a central support surface for a pestle, whereby the support surface is arranged outside the opening of the pressing device in order to enable an undisturbed extrusion motion of the pestle. Moreover, the invention is based on observing, surprisingly, that highly viscous cement pastes as starting components can be extruded from a cartridge with a dispensing tube and static mixers arranged therein by manually actuated extrusion devices, if the cross-section of the tubular cartridge is equal to or smaller than 25 mm.

It is therefore inventive for the internal diameter of the first cartridge to be smaller than, equal to 25 mm and preferably to be smaller than, equal to 20 mm.

The invention is based on the idea to use only one cylindrical external cartridge instead of multiple side-by-side cartridges or coaxial cartridges for separate storage of the two pasty starting components in order to minimise the flow resistance during dispensation. The wall of the internal cartridges being pushed away by means of the pressing device allows even small amounts of the PMMA bone cement to be used and allows even small cartridges with internal spaces with small internal diameters to still be suitable for extrusion.

Own experiments have shown that a very large pressure drop occurs on the static mixer in the dispensing tube during the extrusion process of the cartridges due to the high viscosity of the pasty starting components. The experiments further showed, for a conical dispensing tube with a total length of approx. 17 cm and with an internal diameter of 11 mm on the cartridge head and while using 10 static mixing elements, an extrusion force in excess of 7 kN is required in order to extrude the highly viscous cement pastes at a dispensation rate that is acceptable for a medical user. These investigations led to the devices according to the invention and the methods according to the invention.

Furthermore, the invention is based on observing that highly viscous cement dough can be dispensed through a dispensing tube with static mixer with commercial, manually driven extrusion devices and/or applicators in an acceptable amount of time and with an expenditure of force that is acceptable since it can be applied manually, if the diameter of the dispensing tube on its front side is maximally 25 mm. The design according to the invention provides a storage and mixing system that can realise such small diameters for the application of highly viscous starting components. In this context, the first cartridge and/or the hollow spaces can still be filled with the starting components without too much effort.

An exemplary and particularly preferred storage and mixing system according to the invention for pasty two-component polymethylmethacrylate bone cement is composed of a) a tubular first cartridge, in whose internal space a first cement paste is stored as first starting component (or main starting component);

b) at least one tubular second cartridge that is arranged in the internal space of the first cartridge and is connected to the internal wall of the first cartridge over the entire length of the second cartridge, whereby a second cement paste is stored as second starting component in the internal space of the second cartridge;

c) a cartridge head that can be detached from the first cartridge and the second cartridge and closes one end (or one opening each on the end) of the first cartridge and one end of the second cartridge;

d) a dispensing tube with an attachment means for attachment to the first cartridge, whereby a static mixer is arranged in the dispensing tube;

e) a first dispensing plunger that is arranged in the internal space of the first cartridge such as to be axially mobile;

f) a second dispensing plunger that is arranged in the internal space of the second cartridge such as to be axially mobile;

g) a pressing device that is connected to the first dispensing plunger and possesses an inclined clamping edge that is inclined at an angle of at least 40° particular to the longitudinal axis in the direction of the internal wall of the first cartridge, whereby the clamping edge squeezes the wall of the second cartridge against the internal wall of the first cartridge, whereby the clamping edge covers at least 30% of the surface area of the cross-section of the second cartridge;

h) whereby a gap is formed between the outside of the pressing device and the internal wall of the first cartridge, whereby the gap area and/or the gap dimension is equal to or larger than the cross-sectional area of the squeezed second cartridge;

i) the rear side of the pressing the device is designed as a support surface for a pestle of an extrusion device;

j) the second dispensing device is arranged appropriately in the second cartridge such that the underside of the second dispensing plunger is arranged the head of the pressing device in the direction of the cartridge head; and, k) when the pressing device moves in the direction of the cartridge head, the pressing device squeezes the second cartridge and thus presses the deformed wall of the second cartridge onto the underside of the second dispensing plunger and moves the second dispensing plunger in the direction of the cartridge head.

The pressing device is designed in the form of a type of clamping body by means of which the second cartridge is being deformed and/or is being squeezed against the internal wall of the first cartridge via the clamping edge.

The invention can provide two second cartridges and/or one second and one third cartridge to be arranged in the internal space of the first cartridge. As a result, it is feasible to introduce a third cement component as starting component, for example pharmaceutical agents, into the cement dough. This can be advantageous if pharmaceutical agents are unstable, e.g., with respect to special components of the cement pastes, such as peroxides, over the period of time from the filling to the application of the paste cement and/or of the mixed cement dough. Moreover, this can also be used for the storage of cement pastes with complex initiators systems consisting of multiple components, in which the initiator components need to be stored separately, in the storage and mixing system. In order to provide for a symmetrical application of force to the pressing device during the propulsion of the pressing device in the storage and mixing system, it may make sense, even when a two-component bone cement is used, to have two internal second [cartridges] and/or one internal second and one internal third cartridge arranged in the first cartridge. This can prevent, e.g., the pressing device from lodging.

Preferably, the pressing device or at least the clamping edge is manufactured from metal and/or plastic material and/or glass fibre-reinforced plastic material. Preferably, the pressing device or at least the clamping edge consists of steel, an aluminium alloy, a zinc alloy, polyamide, glass fibre-reinforced polyamide, polyetherketone or polysulfone or combinations of said materials. Ceramics and carbon fibre-containing composites are also conceivable for the design of the pressing device or at least of the clamping edge.

The pasty starting components contain the very volatile monomer, methylmethacrylate, that can be polymerised by radical polymerisation. It is therefore indispensable for the storage of the starting components that the cartridges, the cartridge head, and the dispensing plungers are manufactured from plastic materials that represent a good diffusion barrier for methylmethacrylate. The invention can therefore provide the cartridges, the cartridge head, the separating wall, and the dispensing plungers to be made from plastic material, whereby polyethylene-co-vinylalcohol (EVOH), polybutylene-terephthalate (PBT), polyethylene-terephthalate (PET), and polymethacryl acid methylester-co-acrylonitrile are preferred as plastic materials. In addition, it is also feasible to apply diffusion-proof metal layers, metal or semi-metal oxide layers or plastic layers on the parts that do not contact the starting components. In particular aluminium layers are conceivable as metal layers. In particular silicon dioxide layers are well-suited as semi-metal oxide layers.

The cartridge has, for example, an attachment element for an extrusion device on one end and at least one external thread and/or one internal thread and/or at least one element of a bayonet closure and/or at least one snap-in element of a snap-in closure as connecting element on the opposite end.

The cartridge head can be made up by a rubber-elastic plate and a union cap manufactured from plastic material, whereby the union cap blocks the rubber-elastic plate in upward direction by means of a projecting edge, and whereby two openings that are closed by a stopper are arranged in the rubber-elastic plate.

In a first embodiment, a plastic plate with two openings, which can be closed by stoppers, are arranged in the cartridge head on or under the rubber elastic plate.

The union cap, as connecting element, possesses an internal thread or an external thread or a bayonet closure or snap-in elements for a snap-in-type closure.

According to the invention, a static mixer is arranged in the dispensing tube. An internal thread and/or an external thread and/or elements of a bayonet closure and/or snap-in elements of a snap-in closure are attached as connecting means on the base of the dispensing tube.

In an alternative embodiment, the front face of the cartridge is designed as the cartridge head, whereby two openings, which can be closed by stoppers, penetrate through the front face of the cartridge.

For example a method for mixing the pasty starting components of the pasty polymethylmethacrylate bone cement using the storage and mixing system is also inventive. The method is characterised by the following steps proceeding in the order given:

a) Removing the cartridge head or the closures from the first cartridge or, as the case may be, from the first and second cartridges;

b) connecting the dispensing tube, which contains a static mixer, to the opened first cartridge;

c) connecting the first cartridge to a manually actuatable extrusion device;

d) manual actuation of the extrusion device, whereby the pestle of the extrusion device pushes onto the support surface of the pressing device in the direction of the dispensing tube, whereby the pressing device squeezes the second cartridge against the wall of the first cartridge and moves the second dispensing plunger in the direction of the dispensing tube, and whereby, simultaneously, the pressing device moves the first dispensing plunger in the direction of the dispensing tube;

e) extrusion of the first cement paste (the first starting component) from the first cartridge through axial motion of the first dispensing plunger in the direction of the dispensing tube;

f) extrusion of the second cement paste (of the second starting component) from the first cartridge through an axial motion of the first dispensing plunger in the direction of the dispensing tube from the second cartridge;

g) mixing the first cement paste and the second cement paste using the static mixer in the dispensing tube; and h) dispensing the mixed cement paste (the bone cement dough) from the dispensing tube.

In a variant of said method, an extrusion device driven by compressed air or by electrical current is used instead of the manually driven extrusion device in steps c) and d).

BRIEF DESCRIPTION OF THE DRAWINGS

Further exemplary embodiments of the invention shall be illustrated in the following on the basis of seventeen schematic figures, though without limiting the scope of the invention. In the figures.

DETAILED DESCRIPTION OF THE DISCLOSURE

To some extent, identical or similar components are identified in the figures through the same reference numbers for the purpose of simplicity.

Figure 1:
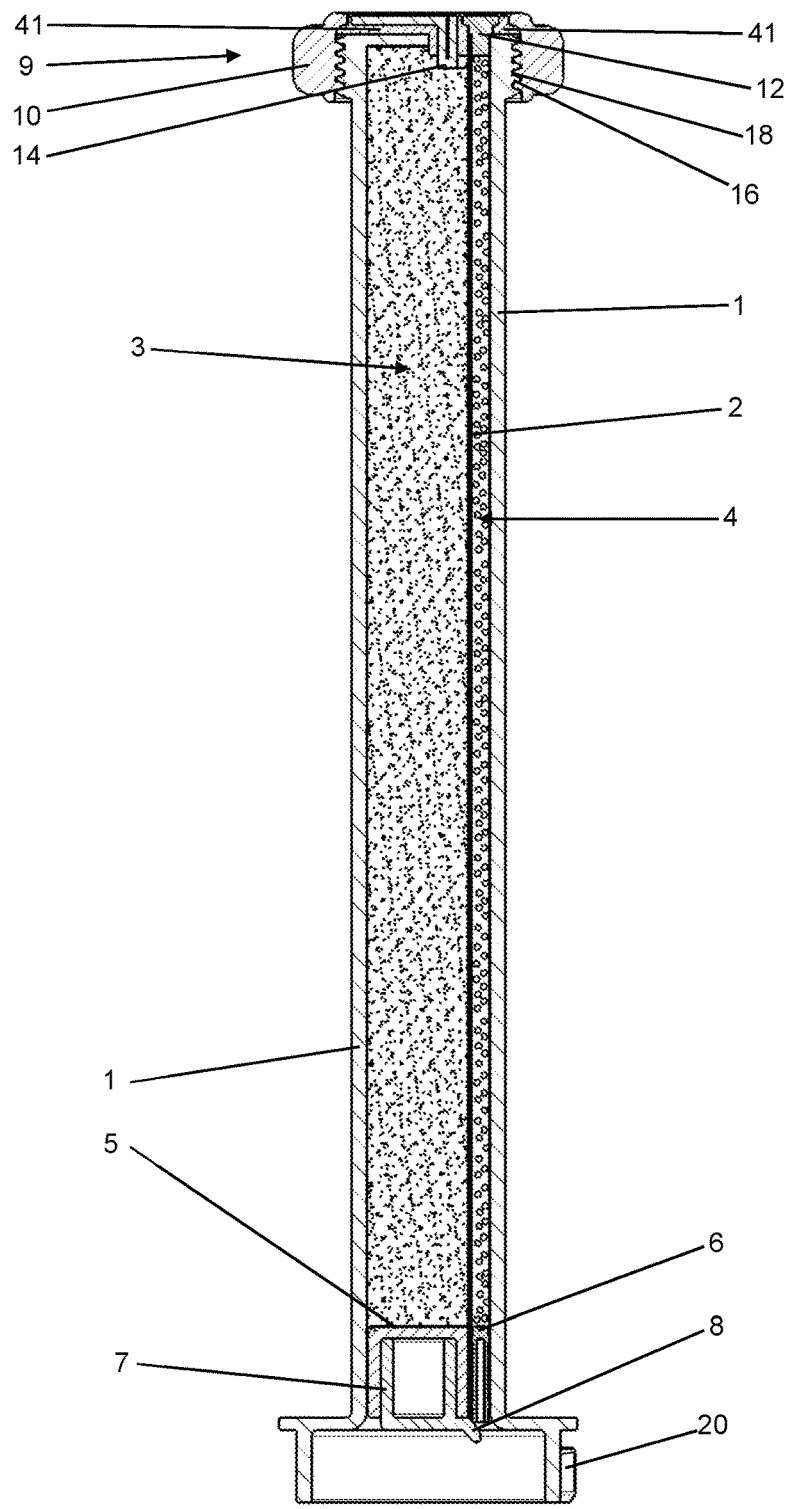
FIG. 1: shows a schematic cross-sectional view of a first exemplary storage and mixing system according to the invention.
Figure 2:
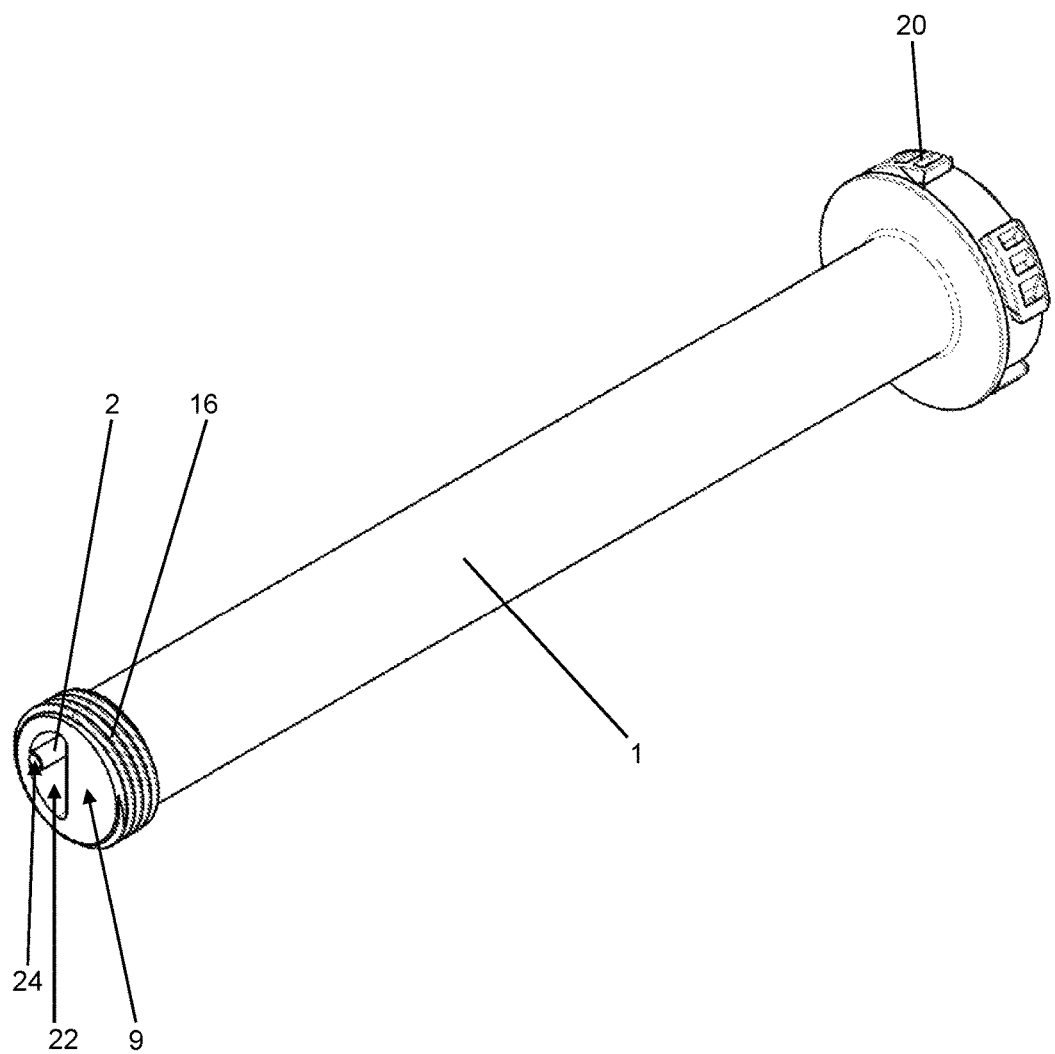
FIG. 2: shows a schematic perspective view of the opened storage and mixing system according to the invention according to FIG. 1.

FIGS. 1 to 5 show a first exemplary embodiment of a storage and mixing system according to the invention. FIG. 1 shows a schematic cross-sectional view of the storage and mixing system according to the invention and FIG. 2 shows a schematic perspective view of the opened storage and mixing system according to the invention according to FIG. 1. The storage and mixing system comprises an external first cartridge 1 that has an internal second cartridge 2 attached to the internal wall of the first cartridge 1 over the entire length of the first cartridge 1. Both cartridges 1, 2 are manufactured from the same material. The wall thickness of the internal second cartridge 2 corresponds to approximately one-fourth of the wall thickness of the external first cartridge 1. Except for the space taken up by the second cartridge 2, the internal space of the first cartridge 1 is filled with a first pasty starting component 3 of a PMMA bone cement. The internal space of the second cartridge 2 is filled with a second pasty starting component 4 of the two-component PMMA bone cement. The internal spaces of the cartridges 1, 2 are limited, on their rear sides (on the bottom in FIGS. 1 and 3 to 5, and on the top in FIG. 2), by a first dispensing plunger 5 in the first cartridge 1 and a second dispensing plunger 6 in the second cartridge 2, whereby the dispensing plungers 5, 6 close off the internal spaces of the cartridges 1, 2 towards the outside in fluid-proof manner. Accordingly, the dispensing plunger 5 of the first cartridge 1 comprises a lateral recess such that it can glide over the second cartridge 2, but also closes off tightly in this place. Matching the smaller internal space, the dispensing plunger 6 of the second cartridge 2 has a smaller diameter than the dispensing plunger 5 of the first cartridge 1.

The internal space of the second cartridge 2 is shaped to be cylindrical with a circular footprint. The internal space of the first cartridge 1 is also shaped to be cylindrical with a circular footprint, whereby the second cartridge 2 takes up a part of the internal space of the first cartridge 1 and thus effects a discontinuation of the circular cylindrical symmetry of the internal space of the first cartridge 1. The dispensing plunger 5 of the first cartridge 1 comprises, on its rear side and/or bottom side (on the bottom in FIGS. 1 and 3 to 5), a depression into which a pressing device 7 is plugged. The pressing device 7 comprises, on its rear side, a clamping edge 8 that engages the space in the internal space of the first cartridge 1 that is occupied by the second cartridge 2, when the pressing device 7 is being propelled forward (upwards in FIGS. 1 and 3 to 5) within the first cartridge 1. The clamping edge 8 comprises a chamfered surface that is inclined in the direction perpendicular to the cylinder axis of the second cartridge 2. The second cartridge 2 has a volume that corresponds to about one-twentieth [of the volume] of the first cartridge 1. Accordingly, the cement dough is mixed from the starting components 3, 4 at a mixing ratio of approximately 20 to 1. Due to the cylindrical symmetry of the internal spaces of the cartridges 1, 2, the mixing ratio remains constant during the extrusion process.

The clamping edge 8 or the entire pressing device 7 consist of and/or are appropriately shaped from a material such that the pressing device 7 or at least the clamping edge 8 is harder or more solid than the wall of the second cartridge 2. Preferably, the clamping edge 8 and the entire pressing device 7 consist of a metal, in particular an aluminium alloy, or a solid plastic material that is at least harder, more solid and/or tougher than the material of the wall of the second internal cartridge 2.

The dispensing plungers 5, 6 are axially supported as in bearings such as to be mobile in longitudinal direction in the internal space of the cartridges 1, 2 in the direction of a cartridge head 9 of the cartridges 1, 2 (from bottom to top in FIGS. 1 and 3 to 5). An opening 22 of the first cartridge 1 and an opening 24 of the second cartridge 2 are provided in the cartridge head 9 (see FIG. 2). In the storage state of the storage and mixing system (see FIG. 1), a union nut 10 is screwed on in the region of the cartridge head 9 and is used to hold a rubber-elastic plate 41 that limits the two openings 22, 24 and forms a part of the cartridge head 9. Two stoppers 12, 14 are plugged into the openings 22, 24 and close the openings 22, 24 and thus close the internal spaces of the cartridges 1, 2 on the front side (on the top in FIG. 1, on the bottom left in FIG. 2, as seen in the direction of the observer) in fluid-proof manner. The opening 22 of the first cartridge 1 is placed appropriately such that it is aligned with and/or adjacent to the opening 24 of the second cartridge number 1. In the areas, which are more distant from the opening 24, the first cartridge 1 is closed off in the area of the cartridge head 9. By this means, the second starting component 4 is being mixed deeper into the flow of the first starting component 3 as early as upon exit from the second cartridge 2. By this means, better mixing of the two starting components 3, 4 is generated.

An external thread 16 is provided on the outside of the front side of the first cartridge 1 as attachment element 16, onto which the union nut 10 can be and/or is screwed. For this purpose, the union nut 10 comprises a matching internal thread 18 as a counter-attachment element 18. A socket with a connector 20 for attachment of an extrusion device (not shown) is provided on the rear side of the storage and mixing system. The extrusion device supports the external first cartridge 1 and comprises a pestle by means of which the pressing device 7 can be pushed in the direction of the cartridge head 9. Preferably, the extrusion device is driven manually.

Figure 3:
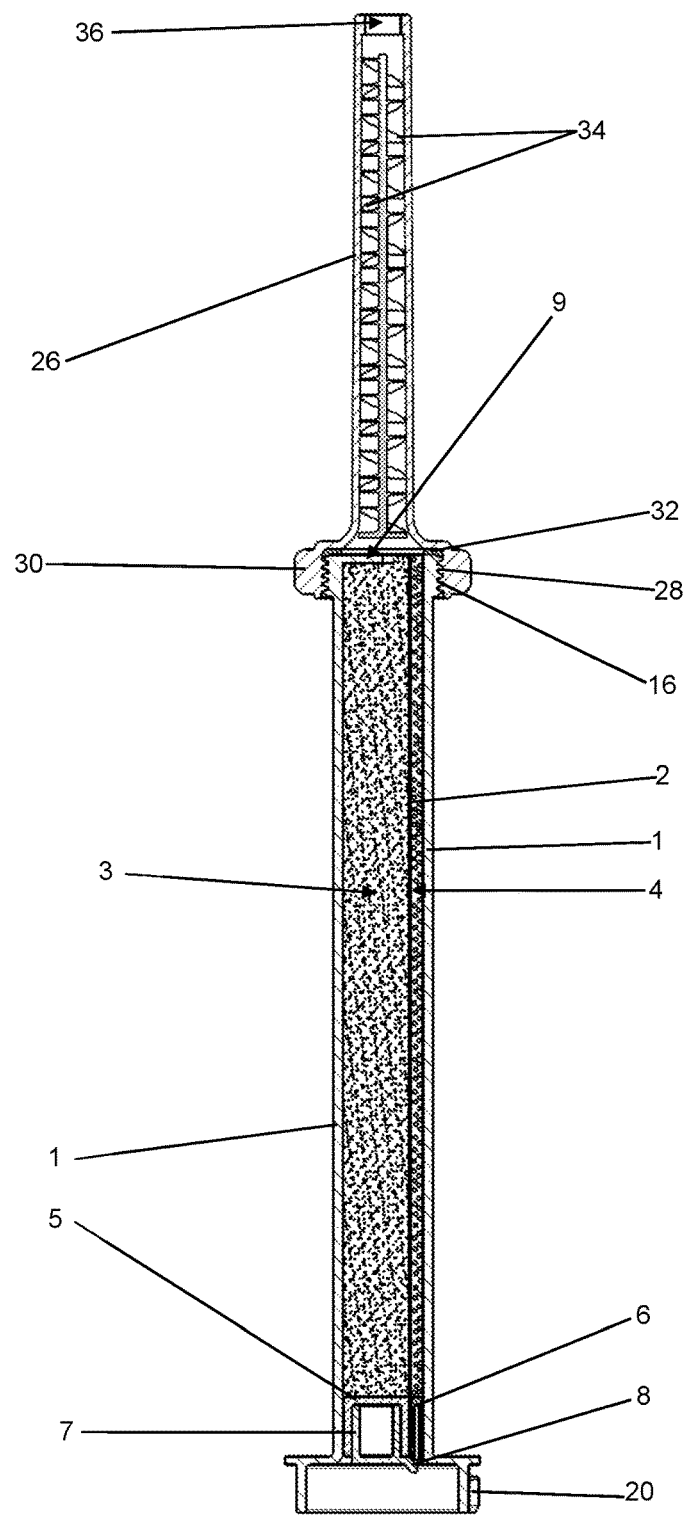
FIG. 3: shows a schematic cross-sectional view through the storage and mixing system according to the invention according to FIGS. 1 and 2 right before the application of the PMMA bone cement, with a dispensing tube attached to it.

FIG. 3 shows a schematic cross-sectional view through the storage and mixing system according to the invention according to FIGS. 1 and 2 right before the application of the PMMA bone cement, with a dispensing tube 26 being attached to the front side of the first cartridge 1. To attach the dispensing tube 26 to the first cartridge 1, the union nut 10 is unscrewed and the stoppers 12, 14 are removed and the cartridges 1, 2 are thus opened. Subsequently, the dispensing tube 26 is screwed onto the external thread 16. For this purpose, an internal thread 28 matching the external thread 16 is provided on the dispensing tube 26 in the region of a socket 30. The dispensing tube 26 is sealed with respect to the storage and mixing system and/or the connector of the first cartridge 1 on the cartridge head 9 by a circumferential seal 32 such that no starting components 3, 4 and no mixed cement dough are/is pushed outwards between the dispensing tube 26 and the cartridge head 9.

Ten static mixers 34 are arranged in the dispensing tube 26 and mix the starting components 3, 4 with each other when these are being pressed through the dispensing tube 26. This produces a well-mixed cement dough that can be dispensed and/or applied via a dispensing opening 36 on the tip of the dispensing tube 26. The dispensing tube 26 can be part of the storage and mixing system according to the invention.

Figure 4:
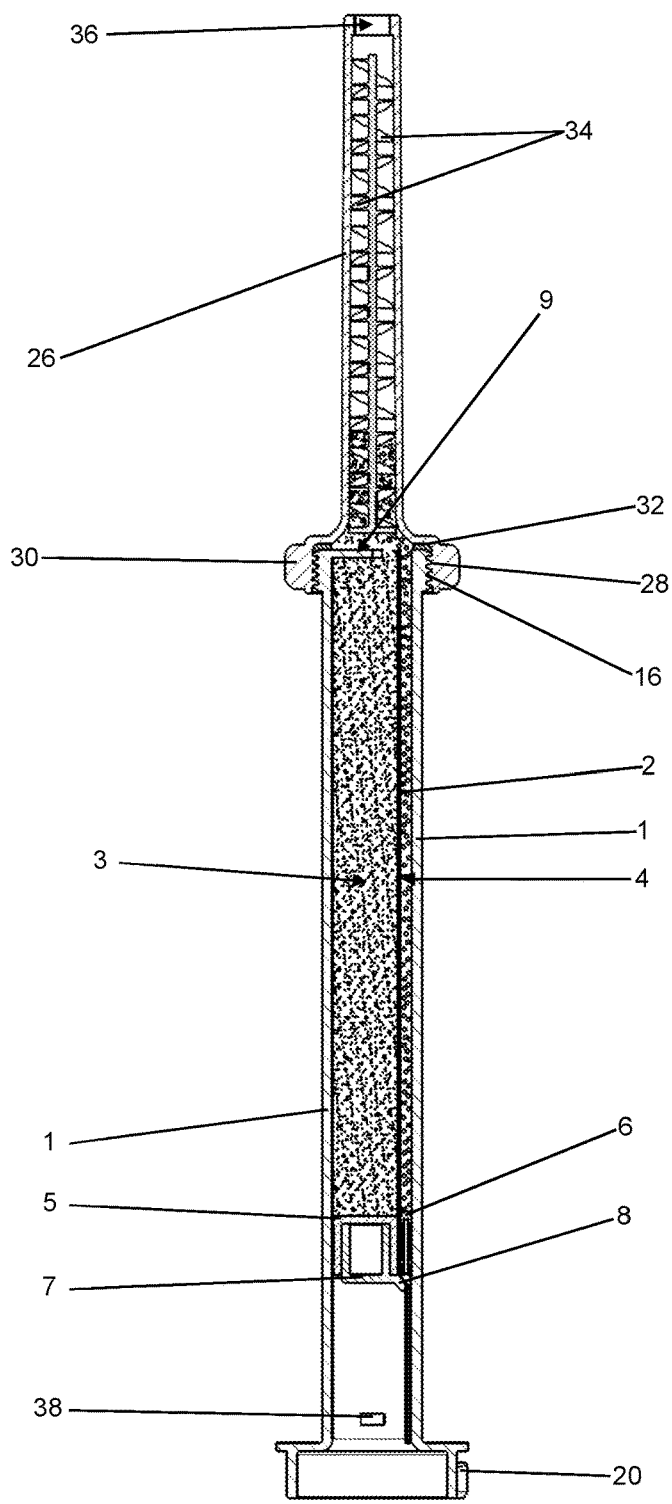
FIG. 4: shows a schematic cross-sectional view through the storage and mixing system according to the invention according to FIG. 3, during the mixing process.
Figure 5:
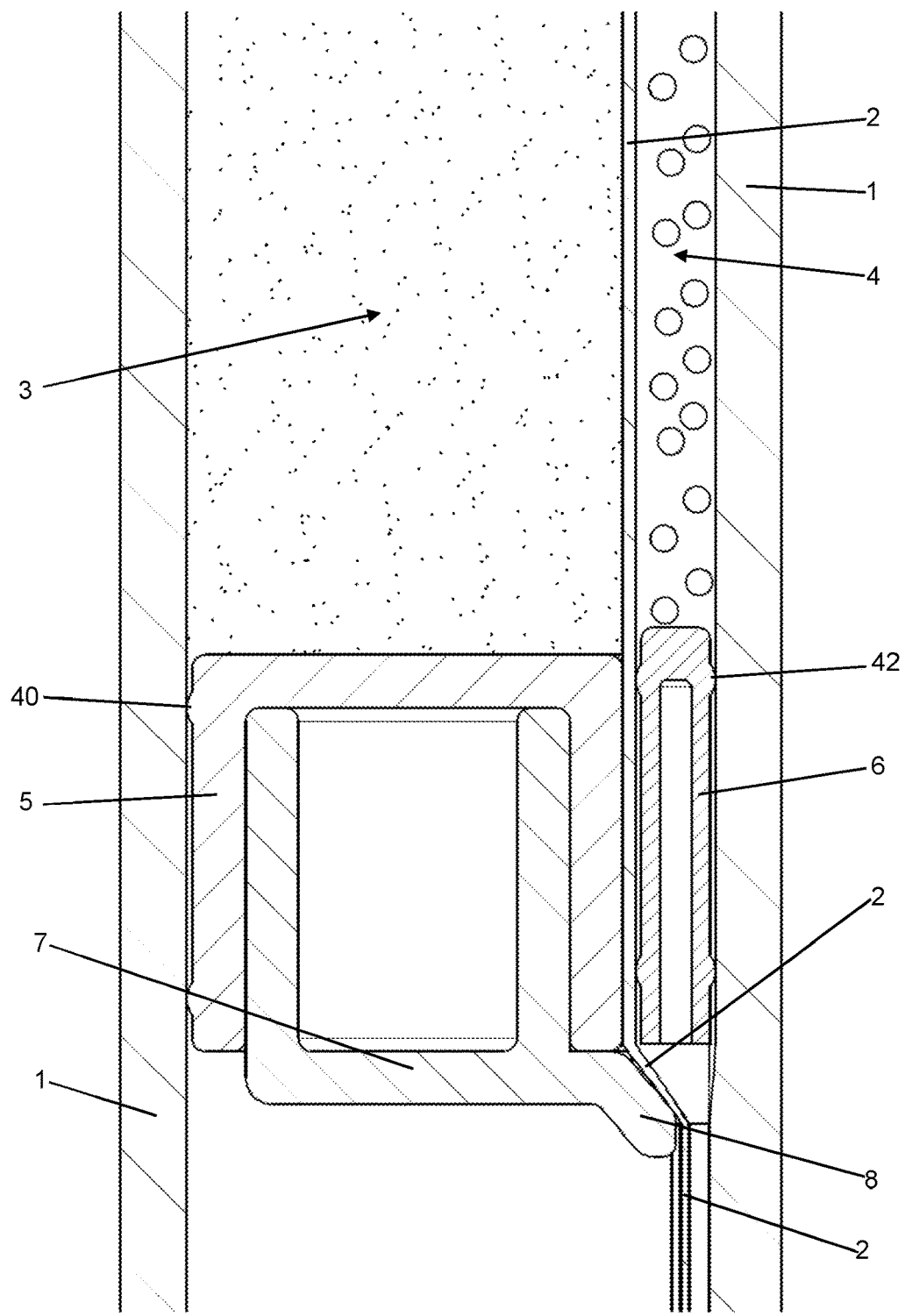
FIG. 5: shows a schematic cross-sectional view of the drive of the storage and mixing system according to the invention according to FIG. 4.

When the dispensing tube 26 is attached to the first cartridge 1, the storage and mixing system is inserted into the extrusion device (not shown) and is connected to the extrusion device by means of the connector 20. The pestle of the extrusion device is driven into the storage and mixing system on the bottom side and thus presses onto the pressing device 7 on the bottom side. Since the first dispensing plunger 5 is connected to the pressing device 7, it is inserted into the first cartridge 1 by the pressing device 7 and, in the process, the first component 3 is pushed from the first cartridge 1 into the dispensing tube 26. Simultaneously, the wall of the second cartridge 2 is pushed in the direction of the internal wall of the first cartridge 1 by the clamping edge 8. Due to the deformation of the wall of the second cartridge 2, the second dispensing plunger 6 is being pushed in the direction of the cartridge head 9 and thus the second starting component 4 in the interior of the second cartridge 2 is pressed into the dispensing tube 26. Said scenario is shown in FIGS. 4 and 5. FIG. 4 shows a schematic cross-sectional view through the storage and mixing system according to the invention according to FIG. 3 during the mixing process, and FIG. 5 shows a magnified schematic cross-sectional view of the drive of the storage and mixing system according to the invention according to FIG. 4.

Two opposite depressions 38 are provided in the internal wall of the external first cartridge 1 as snap-in means 38. Two matching counter-snap-in means (not shown) are provided in the first dispensing plunger 5, at the external jacket surface, and can engage the depressions 38 and thus support the dispensing plunger 5 in the starting position that is suitable for storage of the starting components 3, 4 (see FIG. 1). The snap in-mechanism is detachable by pressing on the rear side of the dispensing plunger 5 and/or on the rear side of the pressing device 7 such that the first dispensing plunger 5, and thus the pressing device 7, can be moved in the direction of the cartridge head 9 when the snap-in resistance is overcome.

Two circumferential elevations 40 are provided on the first dispensing plunger 5 as seals 40 by means of which the dispensing plunger 5 closes off against the internal walls of the first cartridge 1. Likewise, two circumferential elevations 42 are provided on the second dispensing plunger 6 as seals 42 by means of which the dispensing plunger 6 closes off against the internal walls of the second cartridge 2. By means of these seals 40, 42, it can be made sure that the entire content of the two cartridges 1, 2, i.e. the two starting components 3, 4, are expelled completely and can thus be used for producing a PMMA bone cement mixture at the desired ratio. The elevations 40, 42 can also be formed by the sealing rings made of rubber. Since the wall of the second cartridge 2 is compressed by the second dispensing plunger 6 only after the second starting component 4 is expelled, the creases that are generated when the wall of the second cartridge 2 is being compressed do not retain residual amounts of the second starting component 4 and thus the mixing ratio in the cement dough is not being falsified.

Using the inventive design of the storage and mixing system, even very small amounts of the second starting component 4 can be admixed at the correct and/or desired mixing ratio. Conventional extrusion devices with a central pestle can be used for mixing and dispensing the cement dough, since the wall of the second cartridge 2 is being pushed outwards in the direction of the first cartridge 1 and thus is not in the way of the motion of the pestle.

The external first cartridge 1 can be designed to be appropriately narrow, preferable, according to the invention, with an internal diameter of maximally 25 mm or particularly preferably with an internal diameter of maximally 20 mm, such that the viscous starting components 3, 4, in particular the viscous first starting component 3, can be pushed into the dispensing tube 26 and through the static mixers 34 without the resistance of the viscous pastes 3, 4 being so large that these can no longer be expelled with conventional, manually driven extrusion devices.

Figure 6:
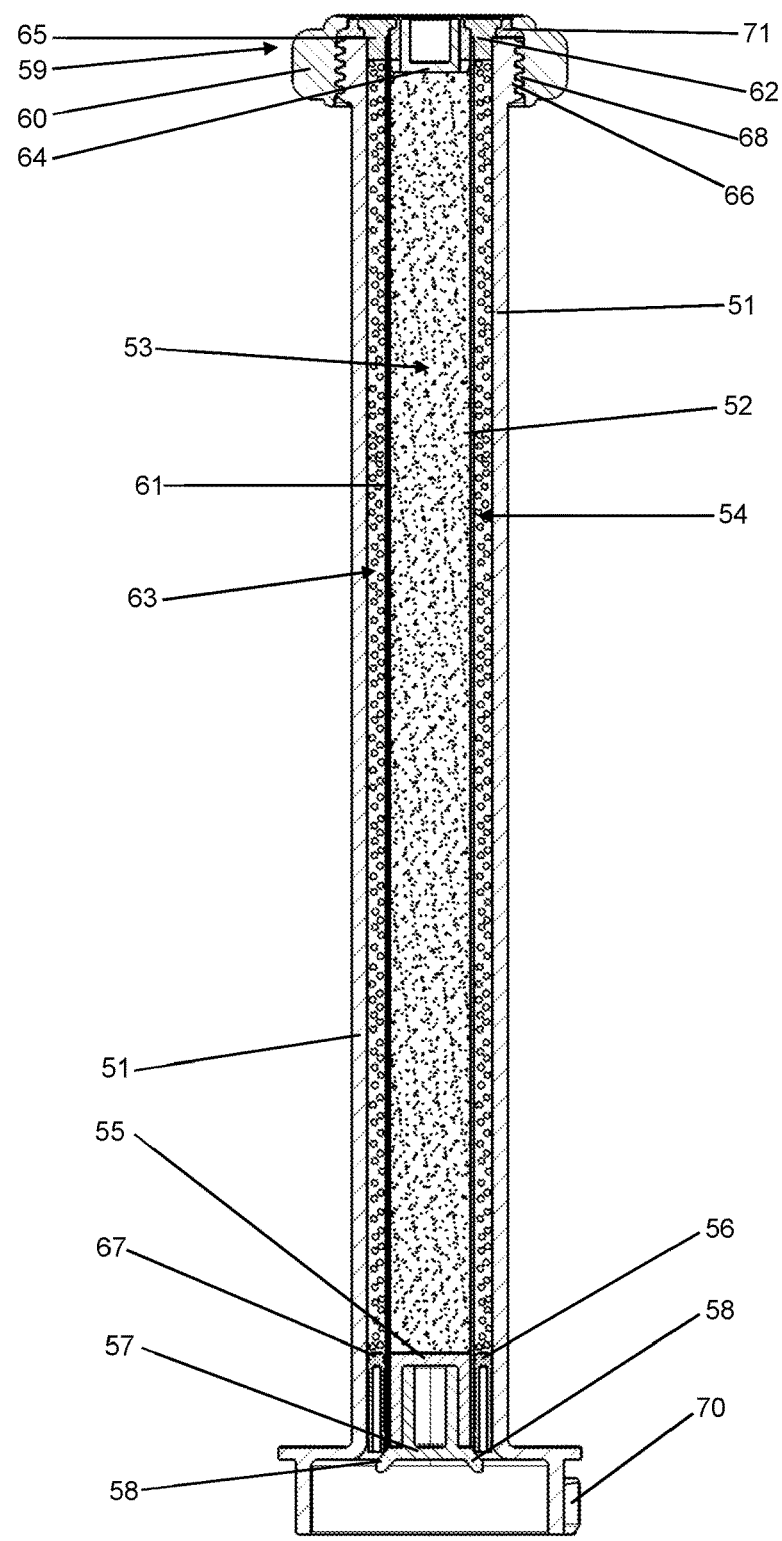
FIG. 6: shows a schematic cross-sectional view of a second alternative storage and mixing system according to the invention.
Figure 7:
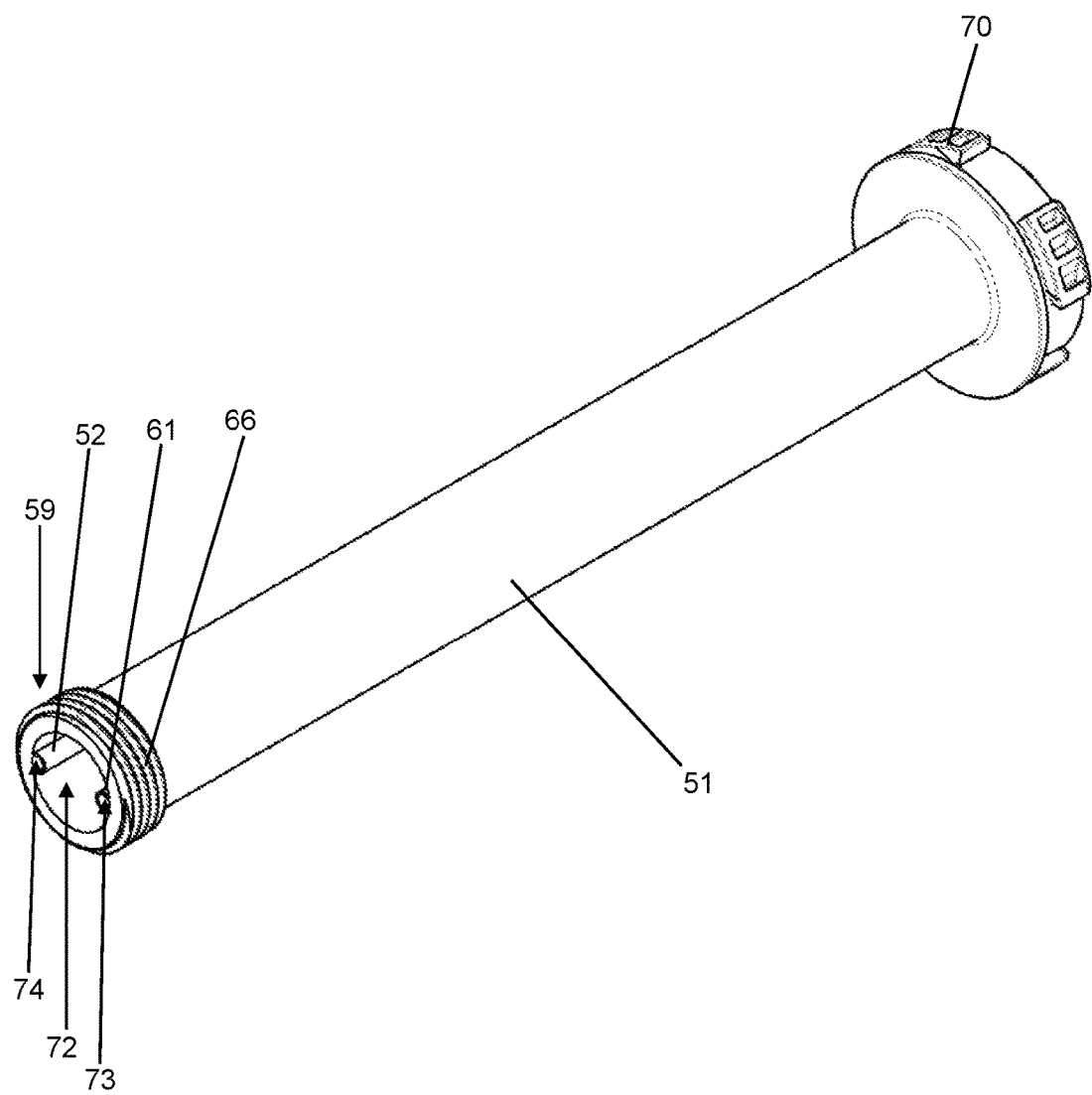
FIG. 7: shows a schematic perspective view of the opened second storage and mixing system according to the invention according to FIG. 6.

FIGS. 6 to 10 show an alternative second exemplary embodiment of a storage and mixing system according to the invention. FIG. 6 shows a schematic cross-sectional view of the storage and mixing system according to the invention and FIG. 7 shows a schematic perspective view of the opened storage and mixing system according to the invention according to FIG. 6. The storage and mixing system comprises an external first cartridge 51 that has an internal second cartridge 52 attached to an internal wall of the first cartridge 51 over the entire length of the first cartridge 51. Moreover, an internal third cartridge number 61 is attached on the opposite internal wall of the first cartridge 51 over the entire length of the first cartridge 51. All three cartridges 51, 52, 61 are manufactured from the same material. The wall thickness of the internal second cartridge 52 and of the internal third cartridge 61 corresponds to approximately one-fourth of the wall thickness of the external first cartridge 51. Except for the space taken up by the second cartridge 52 and the third cartridge 61, the internal space of the first cartridge 51 is filled with a first pasty starting component 53 of a multi-component PMMA bone cement. The internal space of the second cartridge 52 is filled with a second pasty starting component 54 of the multi-component PMMA bone cement. The internal space of the third cartridge 61 is filled with a third pasty starting component 63 of the multi-component PMMA bone cement. The internal spaces of the cartridges 51, 52, 61 are limited, on their rear sides (on the bottom in FIGS. 6 and 8 to 10, and on the top right in FIG. 7), by a first dispensing plunger 55 in the first cartridge 51, a second dispensing plunger 56 in the second cartridge 52, and a third dispensing plunger 67 in the third cartridge 61, whereby the dispensing plungers 56, 56, 67 close off the internal spaces of the cartridges 51, 52, 61 towards the outside in fluid-proof manner. Accordingly, the dispensing plunger 55 of the first cartridge 51 comprises two lateral recesses such that it can glide over the second cartridge 52 and the third cartridge 61. Matching the smaller internal space, the second dispensing plunger 56 of the second cartridge 52 and the third dispensing plunger 67 of the third cartridge 61 have a smaller diameter than the dispensing plunger 55 of the first cartridge 51.

The internal space of the second cartridge 52 and the internal space of the third cartridge 61 are shaped to be cylindrical with a circular footprint. The internal space of the first cartridge 51 is also shaped to be cylindrical with a circular footprint, whereby the second cartridge 52 and the third cartridge 61 take up a part of the internal space of the first cartridge 51 and thus effect a discontinuation of the circular cylindrical symmetry of the internal space of the first cartridge 51. The dispensing plunger 55 of the first cartridge 51 comprises, on its rear side (on the bottom in FIGS. 6 and 8 to 10), a depression into which a pressing device 57 is plugged. The pressing device 57 comprises, on its rear side, two clamping edges 58 and/or one clamping edge 58 that engage(s) the spaces in the internal space of the first cartridge 51 that is occupied by the second cartridge 52 in the third cartridge 61, when the pressing device 57 is being propelled forward (upwards in FIGS. 6 and 8 to 10) within the first cartridge 51. The clamping edges 58 each comprise an inclined surface that is inclined in the direction perpendicular to the cylinder axis of the second cartridge 52 and third cartridge 61. The second cartridge 52 and the third cartridge 61 have volumes of the same size and together have a volume that corresponds to approximately one-twentieth of [the volume of] the first cartridge 51. Accordingly, the cement dough is mixed from the three starting components 53, 54, 63 at a mixing ratio of approximately 40 to 1 to 1. Due to the cylindrical symmetry of the internal spaces of the cartridges 51, 52, 61, the mixing ratio remains constant during the extrusion process.

Instead of a third starting components 63, the second component 54 can also be contained both in the second cartridge 52 and in the third cartridge 61. By this means, a two-component bone cement is mixed at a mixing ratio of 20 to 1. The advantage as compared to the first exemplary embodiment is that, due to the symmetrical design, no forces acting perpendicular to the cylinder axis and/or symmetry axis can be generated during the dispensation of starting components 51, 52, due to which the pressing device 57 might get lodged and thus get impeded in its motion.

The clamping edge 58 or the entire pressing device 57 consist of and/or are appropriately shaped from a material such that the pressing device 57 or at least the clamping edge 58 is harder or more solid than the wall of the second cartridge 52 and the wall of the third cartridge 61. Preferably, the clamping edge 58 and the entire pressing device 57 consist of a metal, in particular an aluminium alloy, or a solid plastic material that is at least harder, more solid and/or tougher than the material of the wall of the second internal cartridge 52 and of the third internal cartridge 61.

The dispensing plungers 55, 56, 67 are axially supported as in bearings such as to be mobile in longitudinal direction in the internal space of the cartridges 51, 52, 61 in the direction of a cartridge head 59 of the cartridges 51, 52, 61 (from bottom to top in FIGS. 6 and 8 to 10). An opening 72 of the first cartridge 51, an opening 74 of the second cartridge 52, and an opening 73 of the third cartridge 61 are provided in the cartridge head 59 (see FIG. 7). In the storage state of the storage and mixing system (see FIG. 6), a union nut 60 is screwed on in the region of the cartridge head 59 and is used to hold a rubber-elastic plate 71 that limits the three openings 72, 73, 74 and forms a part of the cartridge head 59. Three stoppers 62, 64, 65 are plugged into the three openings 72, 73, 74 and close the openings 72, 73, 74 and thus close the internal spaces of the cartridges 51, 52, 61 on the front side (on the top in FIG. 6, on the bottom left in FIG. 7, as seen in the direction of the observer) in fluid-proof manner.

An external thread 66 is provided on the outside of the front side of the first cartridge 51 as attachment element 66, onto which the union nut 60 can be screwed. For this purpose, the union nut 60 comprises a matching internal thread 68 as a counter-attachment element 68. A socket with a connector 70 for attachment of an extrusion device (not shown) is provided on the rear side of the storage and mixing system. The extrusion device supports the external first cartridge 51 and comprises a pestle by means of which the pressing device 57 can be pushed in the direction of the cartridge head 59. Preferably, the extrusion device is driven manually.

Figure 8:
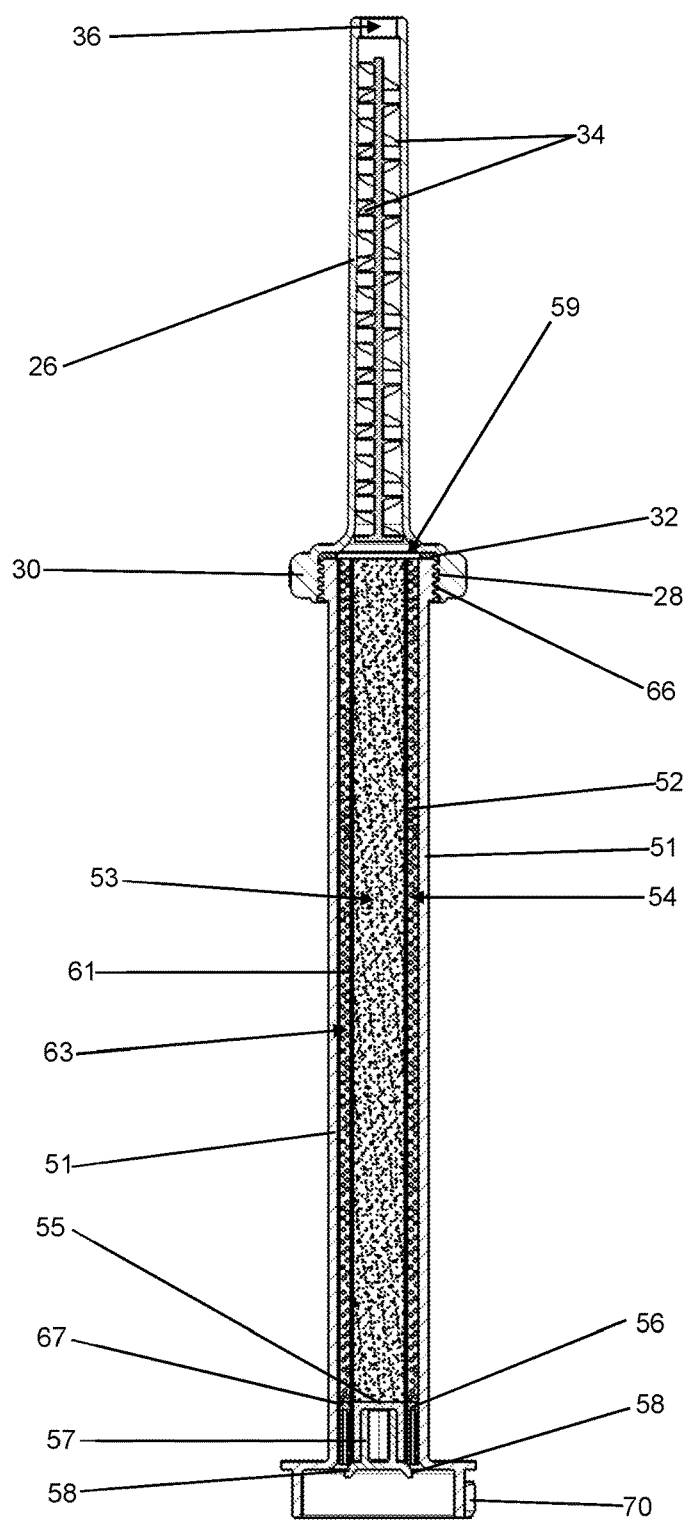
FIG. 8: shows a schematic cross-sectional view through the second storage and mixing system according to the invention according to FIGS. 6 and 7 right before the application of the PMMA bone cement, with a dispensing tube attached to it.

FIG. 8 shows a schematic cross-sectional view through the second storage and mixing system according to the invention according to FIGS. 6 and 7 right before the application of the PMMA bone cement, with a dispensing tube 26 being attached to the front side of the first cartridge 51. To attach the dispensing tube 26 to the first cartridge 51, the union nut 60 is unscrewed and the stoppers 62, 64, 65 are removed and the cartridges 51, 52, 61 are thus opened. Subsequently, the dispensing tube 26 is screwed onto the external thread 66. For this purpose, an internal thread 28 matching the external thread 66 is provided on the dispensing tube 26 in the region of a socket 30. The dispensing tube 26 is sealed with respect to the storage and mixing system and/or the connector of the first cartridge 51 on the cartridge head 59 by a circumferential seal 32 such that no starting components 53, 54, 63 and no mixed cement dough are/is pushed outwards between the dispensing tube 26 and the cartridge head 59.

Ten static mixing elements 34 are arranged in the dispensing tube 26 and mix the starting components 53, 54, 63 with each other when these are being pressed through the dispensing tube 26. This produces a well-mixed cement dough that can be dispensed and/or applied via a dispensing opening 36 on the tip of the dispensing tube 26. The dispensing tube 26 can be part of the second storage and mixing system according to the invention. The dispensing tube 26 is identical to the dispensing tube 26 described in the context of the first exemplary embodiment according to FIGS. 1 to 5.

Figure 9:
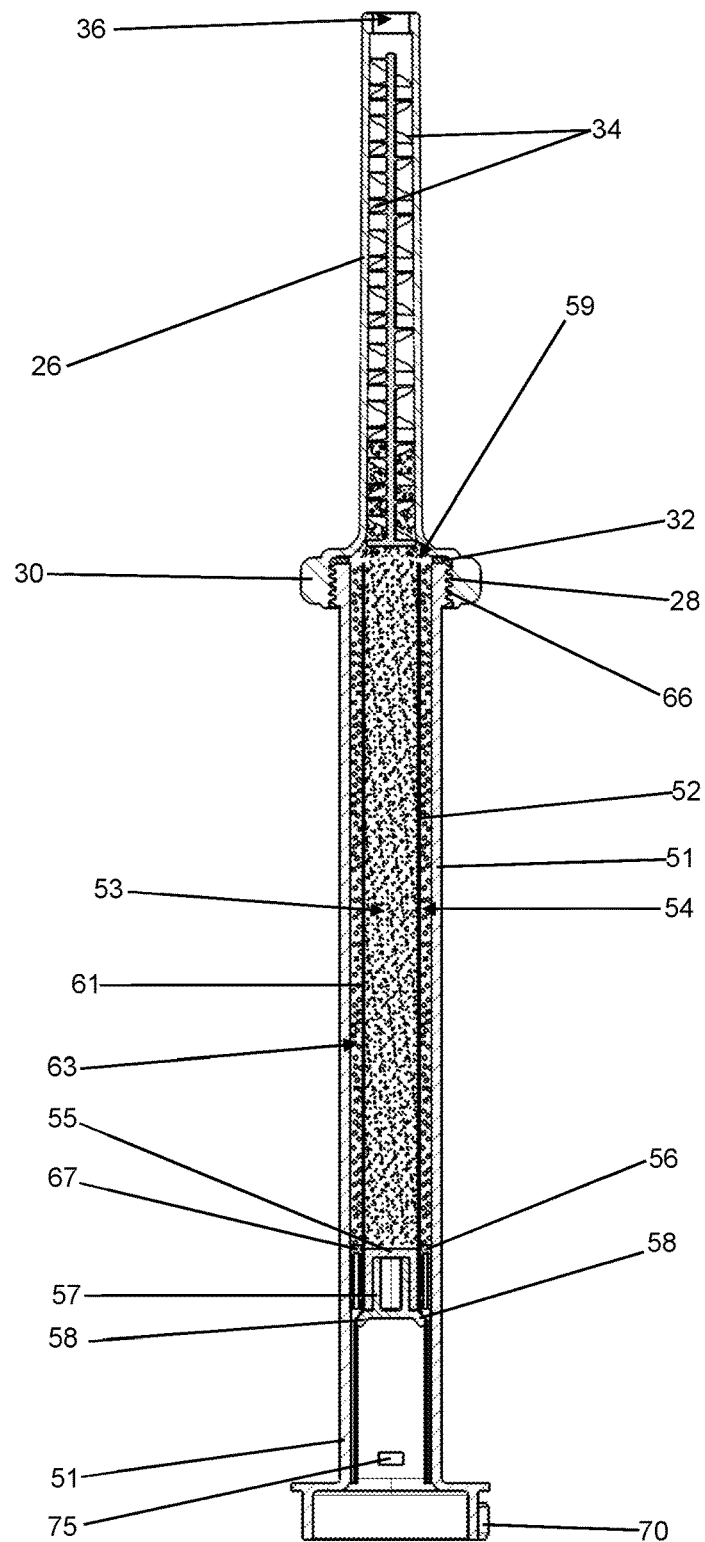
FIG. 9: shows a schematic cross-sectional view through the second storage and mixing system according to the invention according to FIG. 8, during the mixing process.
Figure 10:
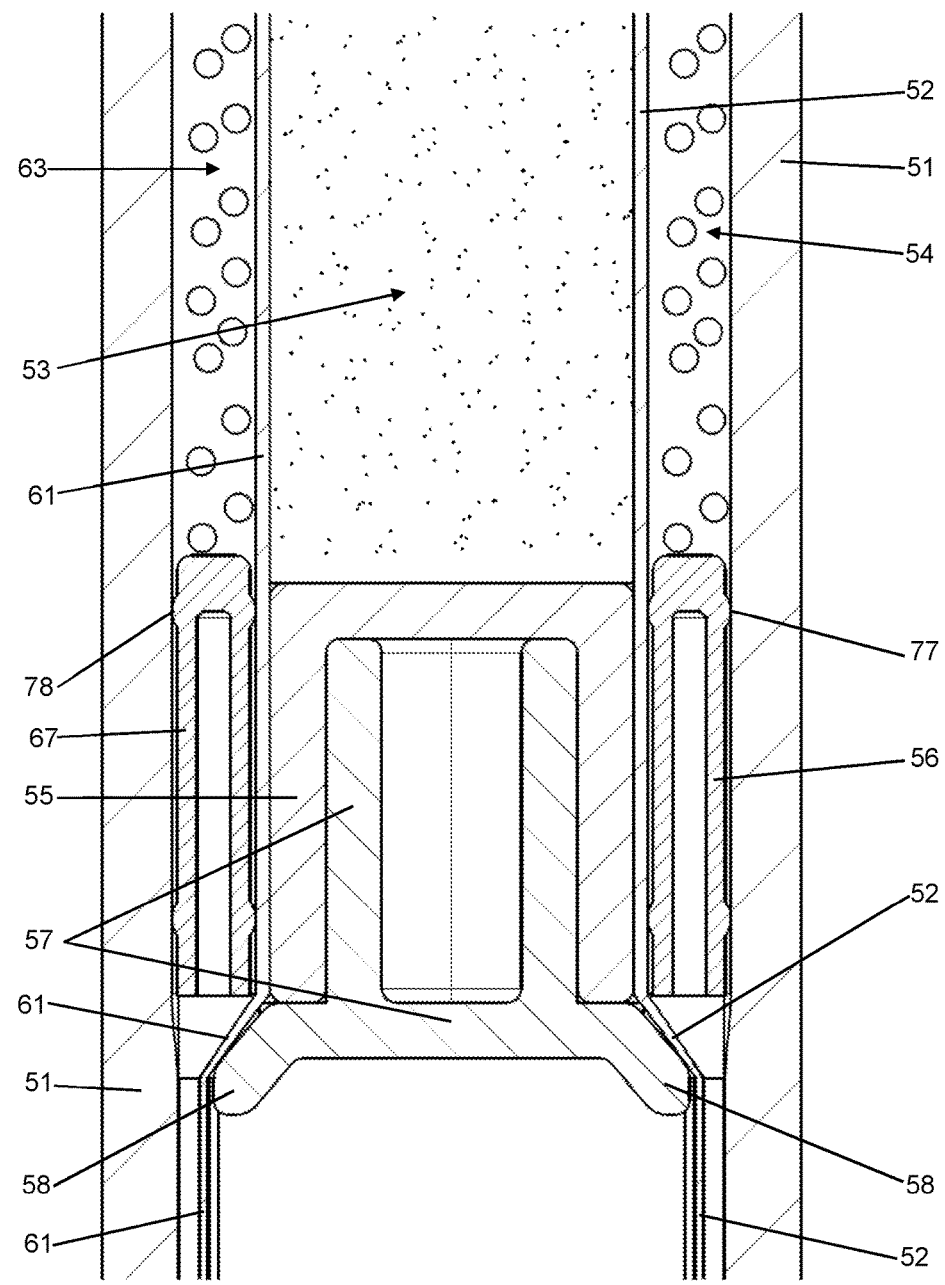
FIG. 10: shows a magnified schematic cross-sectional view of the drive of the second storage and mixing system according to the invention according to FIG. 9.

When the dispensing tube 26 is attached to the first cartridge 51, the storage and mixing system is inserted into the extrusion device (not shown) and is connected to the extrusion device by means of the connector 70. The pestle of the extrusion device is driven into the storage and mixing system on the bottom side and thus presses onto the pressing device 57 on the bottom side. Since the first dispensing plunger 55 is connected to the pressing device 57, it is inserted into the first cartridge 51 by the pressing device 57 and, in the process, the first component 53 is pushed from the first cartridge 51 into the dispensing tube 26. Simultaneously, the wall of the second cartridge 52 and the wall of the third cartridge 61 are pushed in the direction of the internal wall of the first cartridge 51 by the clamping edge 58 and the opposite clamping edge 58, respectively. Due to the deformation of the wall of the second cartridge 52, the second dispensing plunger 56 is being pushed in the direction of the cartridge head 59 and thus the second starting component 54 in the interior of the second cartridge 52 is pressed into the dispensing tube 26. Likewise, due to the deformation of the wall of the third cartridge 61, the third dispensing plunger 67 is being pushed in the direction of the cartridge head 59 and thus the third starting component 63 in the interior of the third cartridge 61 is pressed into the dispensing tube 26. Said scenario is shown in FIGS. 9 and 10. FIG. 9 shows a schematic cross-sectional view through the second storage and mixing system according to the invention according to FIG. 8 during the mixing process, and FIG. 10 shows a magnified schematic cross-sectional view of the drive of the second storage and mixing system according to the invention according to FIG. 9.

Two circumferential elevations are provided on the first dispensing plunger 55 as seals (not shown in FIG. 10, but analogous to the embodiment according to FIG. 5), by means of which the dispensing plunger 65 closes off against the internal walls of the first cartridge 51. Likewise, two circumferential elevations 77 are provided on the second dispensing plunger 56 as seals 77 by means of which the second dispensing plunger 56 closes off against the internal walls of the second cartridge 52. Moreover, two circumferential elevations 78 are provided on the third dispensing plunger 67 as seals 78 by means of which the third dispensing plunger 67 closes off against the internal walls of the third cartridge 61. By means of these seals 77, 78, it can be made sure that the entire content of the three cartridges 51, 52, 61, i.e. the three starting components 53, 54, 63, are expelled completely and can thus be used for producing a PMMA bone cement mixture at the desired ratio. Since the wall of the second cartridge 52 is compressed by the second dispensing plunger 56 only after the second starting component 54 is expelled and the wall of the third cartridge 61 is compressed by the third dispensing plunger 67 only after the third starting component 63 (or, alternatively, the second starting component 54) is expelled, the creases that are generated when the wall of the second cartridge 52 and the wall of the third cartridge 61 are being compressed do not retain residual amounts of the second starting component 54 and of the third starting component 63 and thus the mixing ratio in the cement dough is not being falsified.

Two opposite depressions 75 are provided in the internal wall of the external first cartridge 51 as snap-in means 75. Two matching counter-snap-in means (not shown) are provided in the first dispensing plunger 55, at the external jacket surface, and can engage the depressions 75 and thus support the dispensing plunger 55 in the starting position that is suitable for storage of the starting components 53, 54, 63 (see FIG. 6). The snap in-mechanism is detachable by pressing on the rear side of the dispensing plunger 55 and/or on the rear side of the pressing device 57 such that the first dispensing plunger 55, and thus the pressing device 57, can be moved in the direction of the cartridge head 59 when the snap-in resistance is overcome.

Using the inventive design of the storage and mixing system, even very small amounts of the second starting component 54 and of the third starting components 63 can be admixed at the correct and/or desired mixing ratio. Conventional extrusion devices with a central pestle can be used for mixing and dispensing the cement dough, since the walls of the second cartridge 52 and of the third cartridge 61 are being pushed outwards in the direction of the first cartridge 51 and thus are not in the way of the motion of the pestle.

The external first cartridge 51 can be designed to be appropriately narrow, preferable, according to the invention, with an internal diameter of maximally 25 mm or particularly preferably with an internal diameter of maximally 20 mm, such that the viscous starting components 53, 54, 63, in particular the viscous first starting component 53, can be pushed into the dispensing tube 26 and through the static mixers 34 without the resistance of the viscous pastes 53, 54, 63 being so large that these can no longer be expelled with conventional, manually driven extrusion devices.

Figure 11:
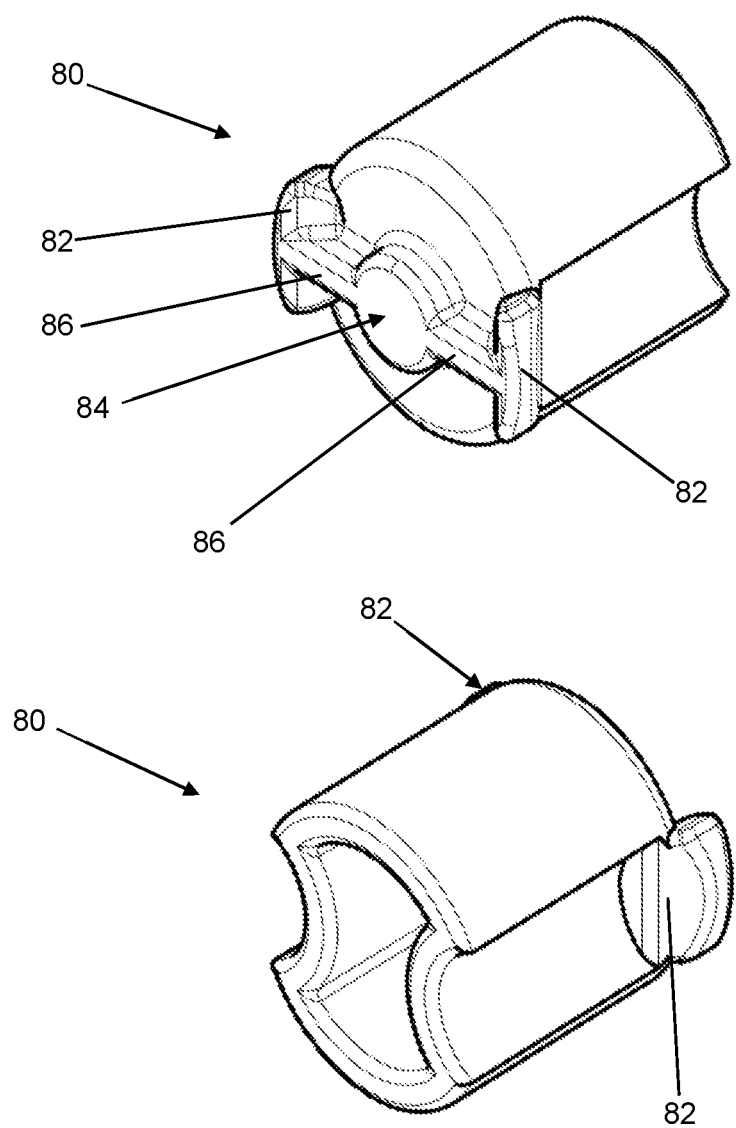
FIG. 11: shows two schematic perspective views of a pressing device for a storage and mixing system according to the invention having two internal cartridges.

FIG. 11 shows two schematic perspective views of a pressing device 80 for a storage and mixing system according to the invention with two internal cartridges, namely on the rear side (top) and on the front side (bottom). The pressing device 80 comprises two chamfered clamping edges 82 by means of which the walls of a second and a third cartridge in the interior of an external first cartridge can be pushed away to the side (analogous to the second exemplary embodiment according to FIGS. 6 to 10). A pressing surface 84 is located on the rear side of the pressing device 80 and provides a support for the pestle of an extrusion device (not shown) for pushing the pressing device 80 into a cartridge. Moreover, the rear side of the pressing device 80 has a fin 86 provided on it that connects the two bottom-side ends of the clamping edges 82 and the projecting support surface 84 and provides for mechanical stabilisation of the shape of the pressing device 80. This design stabilises the position and the orientation of the clamping edges 82. As a result, the walls of the second and third cartridges can be deformed more easily.

Figure 12:
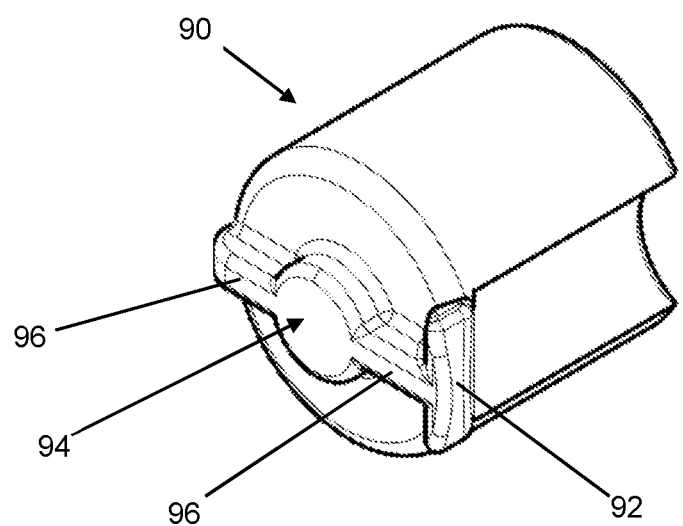
FIG. 12: shows a schematic perspective view of a pressing device for a storage and mixing system according to the invention having one internal cartridge.

FIG. 12 shows a schematic perspective view of a pressing device 90 for a storage and mixing system according to the invention with an internal cartridge, like the first exemplary embodiment shown according to FIGS. 1 to 5. The pressing device 90 comprises a chamfered clamping edge 92 by means of which the walls of a second in the interior of an external first cartridge can be pushed away to the side (analogous to the first exemplary embodiment according to FIGS. 1 to 5). A pressing surface 94 is located on the rear side of the pressing device 90 and provides a support for the pestle of an extrusion device (not shown) for pushing the pressing device 90 into a cartridge. Moreover, the rear side of the pressing device 90 has a fin 96 provided on it that connects the bottom-side end of the clamping edge 92 and the projecting support surface 94 and provides for mechanical stabilisation of the shape of the pressing device 90. This design stabilises the position and the orientation of the clamping edge 92. As a result, the walls of the second cartridge can be deformed more easily.

Figure 13:
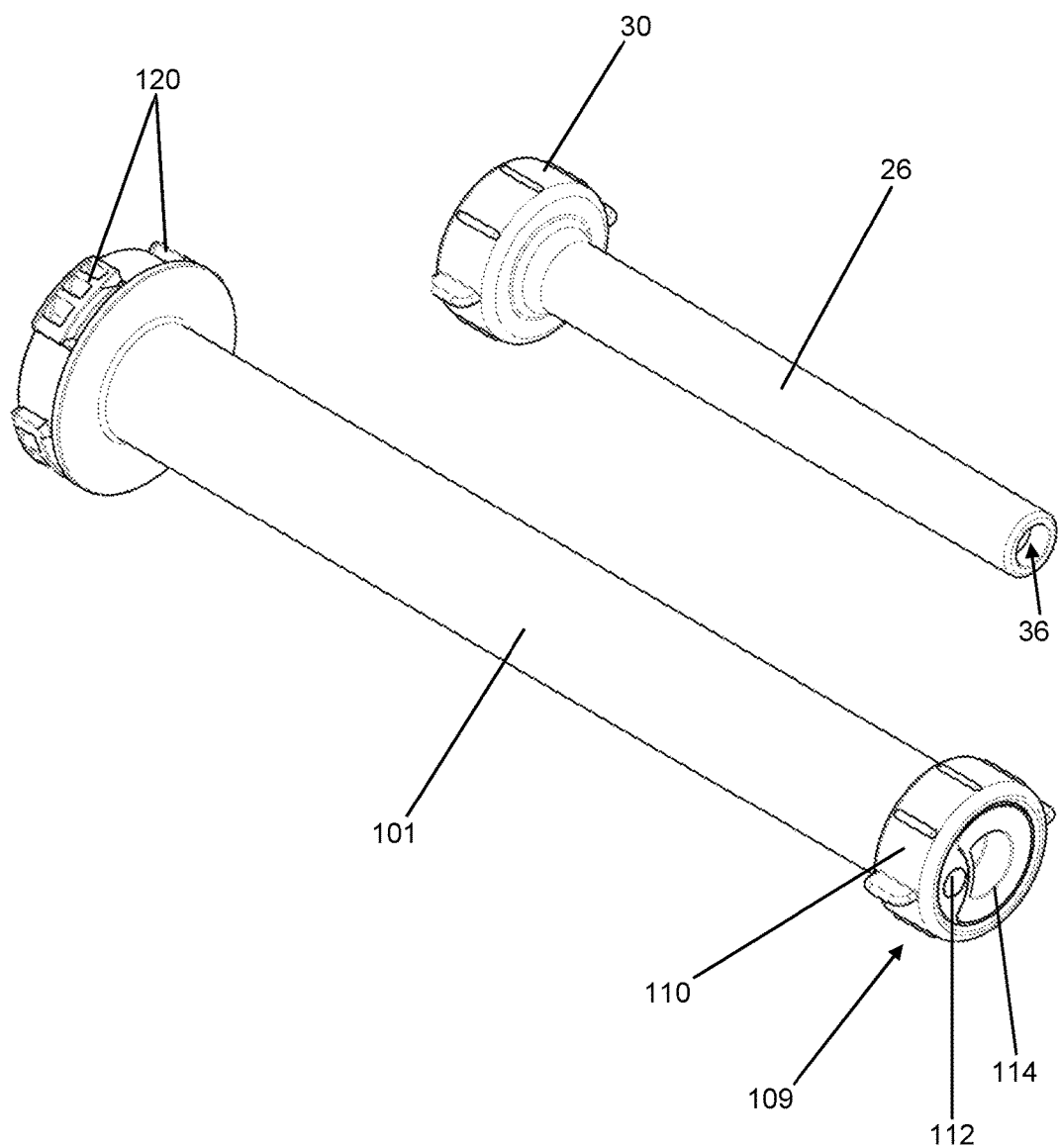
FIG. 13: shows a schematic perspective view of a third alternative storage and mixing system according to the invention.
Figure 14:
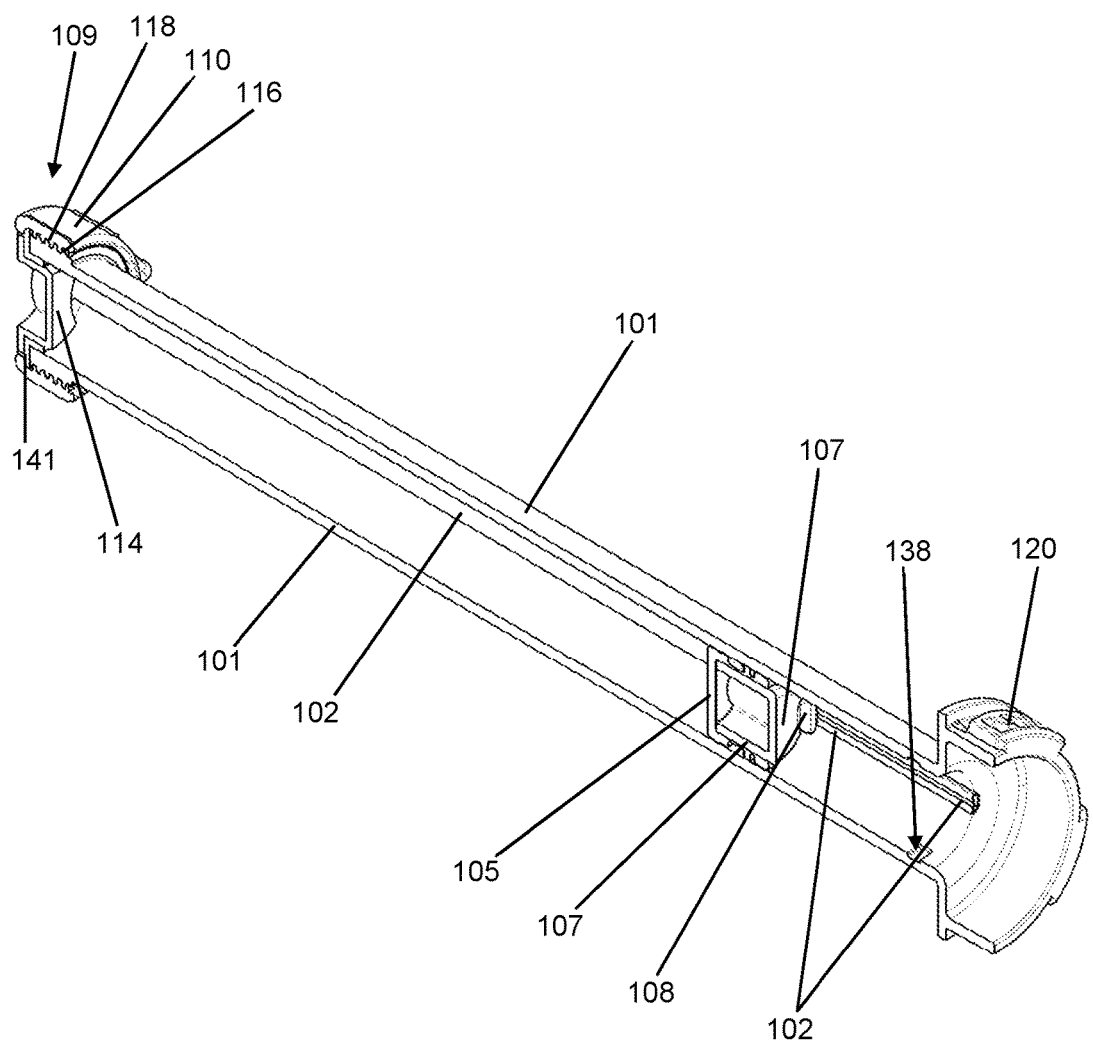
FIG. 14: shows a schematic perspective cross-sectional view of the third storage and mixing system according to the invention according to FIG. 13, with inserted pressing device.
Figure 15:
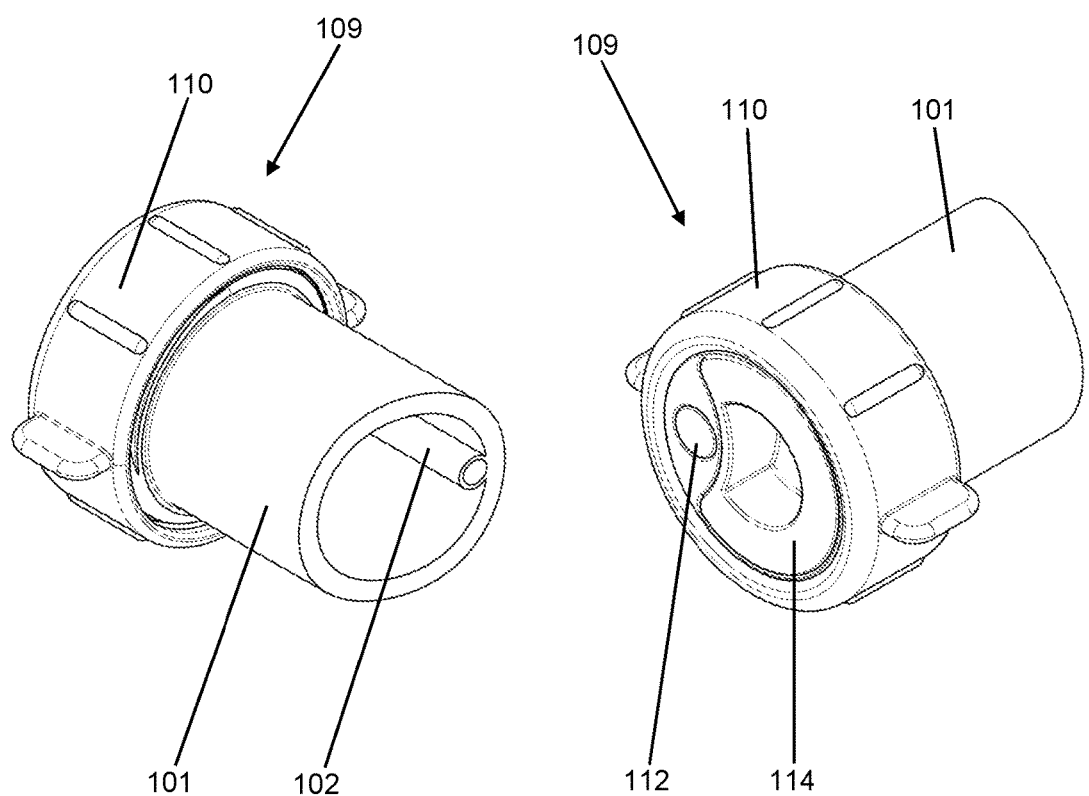
FIG. 15: shows two schematic perspective sectional views of the front region of the third storage and mixing system according to the invention according to FIGS. 13 and 14.
Figure 16:
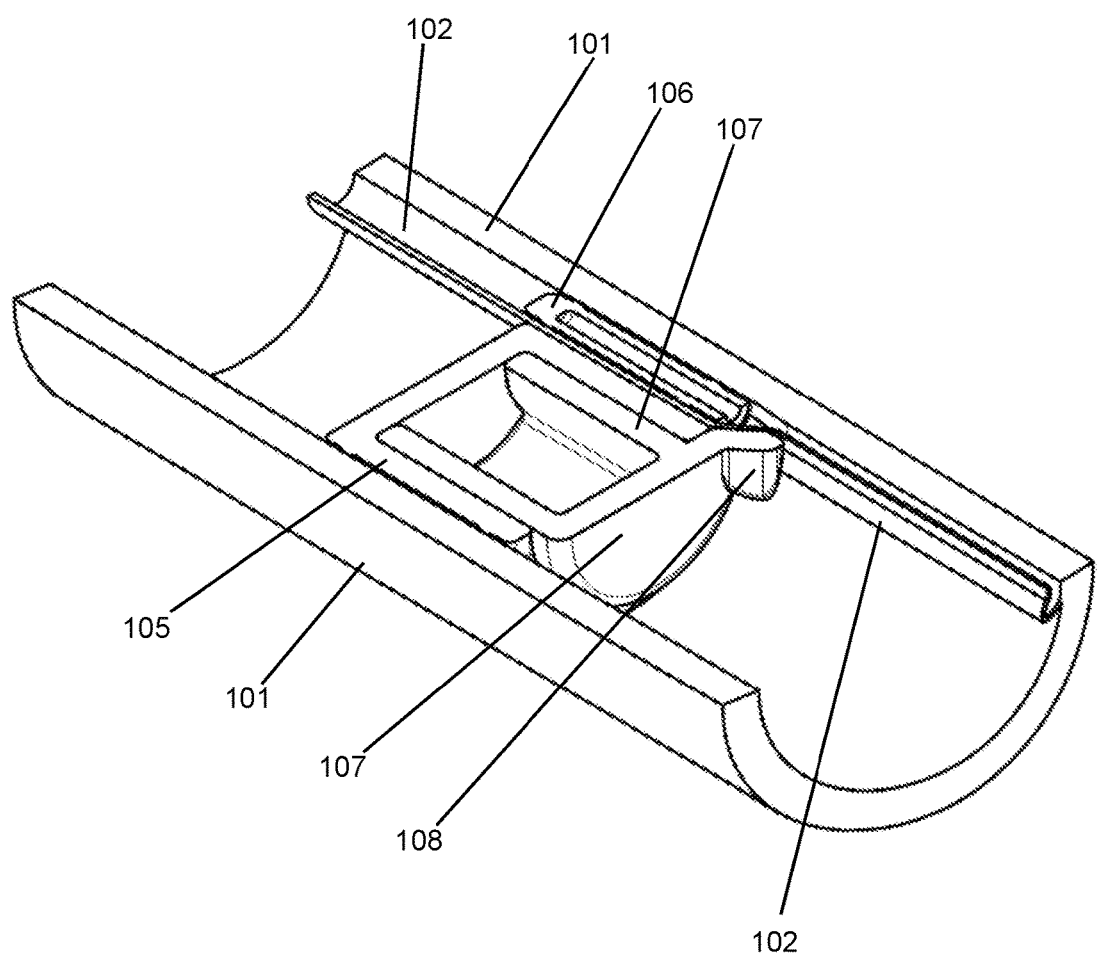
FIG. 16: shows a magnification of a part of the third storage and mixing system according to the invention according to FIGS. 13 to 15 in the form of a schematic perspective cross-sectional view.
Figure 17:
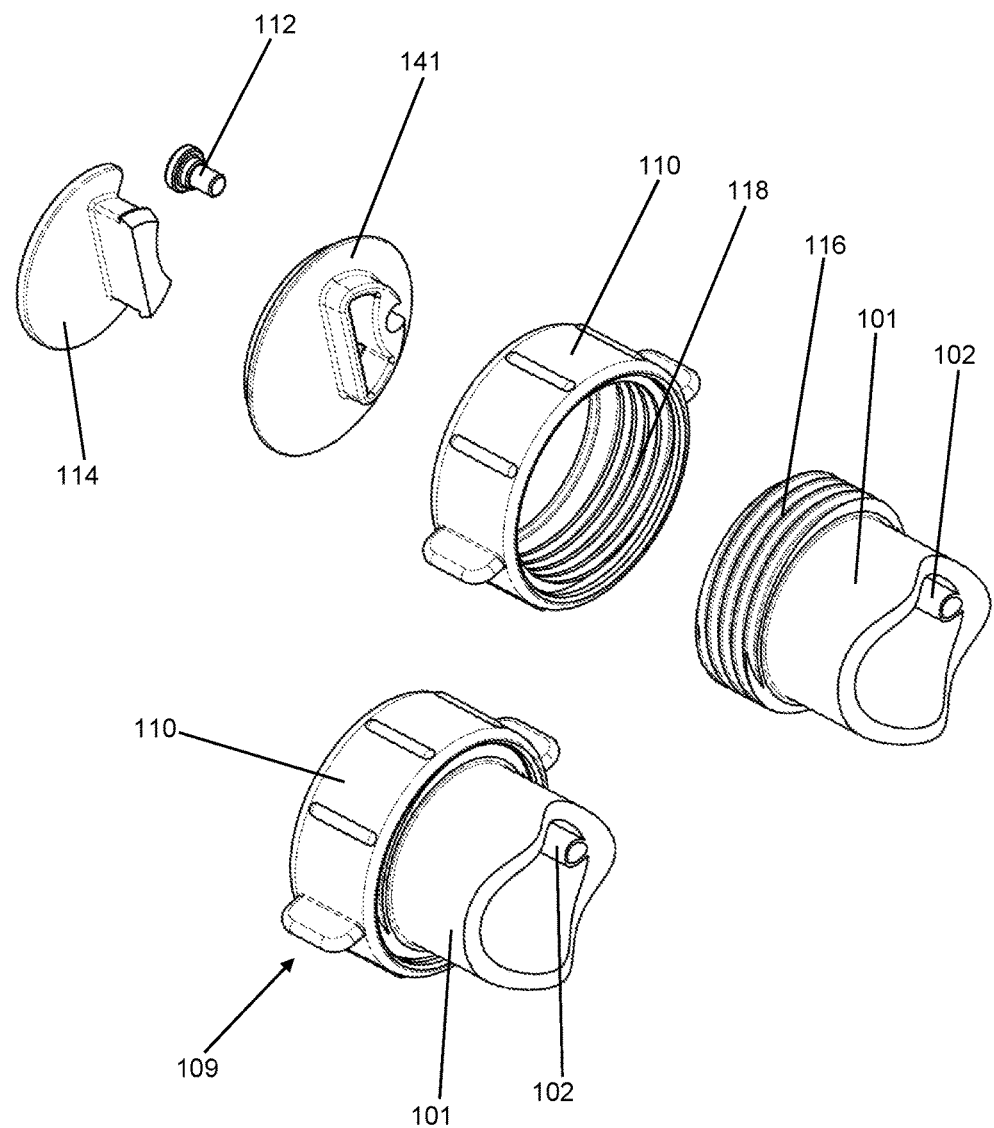
FIG. 17: shows an exploded view (top) and a sectional view (bottom) of the front part of the third storage and mixing system according to the invention according to FIG. 15.

FIGS. 13 to 17 show a third exemplary embodiment of a storage and mixing system according to the invention. In this context, FIG. 13 shows a schematic perspective view of the third, alternative storage and mixing system according to the invention and FIG. 14 shows a schematic perspective cross-sectional view of the third storage and mixing system according to the invention according to FIG. 13 with inserted pressing device 107. FIG. 15 shows two schematic perspective sectional views of the front region of the third storage and mixing system according to the invention according to FIGS. 13 and 14, FIG. 16 shows a magnification of a part of the third storage and mixing system according to the invention according to FIGS. 13 to 15 as a schematic perspective cross-sectional view, and FIG. 17 shows an exploded view (top) and a sectional view (bottom) of the front region of the third storage and mixing system according to the invention according to FIG. 15.

Analogous to the first exemplary embodiment according to FIGS. 1 to 5, the third alternative storage and mixing system according to FIGS. 13 to 17 comprises an external first cartridge 101 that has an internal second cartridge 102 attached to the internal wall of the first cartridge 101 over the entire length of the first cartridge 101. Both cartridges 101, 102 are manufactured from the same material. The wall thickness of the internal second cartridge 102 corresponds to approximately one-fourth of the wall thickness of the external first cartridge 101. Except for the space taken up by the second cartridge 102, the internal space of the first cartridge 101 is filled with a first pasty starting component (not shown) of a PMMA bone cement or can be filled with said first pasty starting component. The internal space of the second cartridge 102 is filled with a second pasty starting component (not shown) of the two-component PMMA bone cement or can be filled with said second pasty starting component. Accordingly, the starting components do not need to be contained in the storage and mixing system.

The internal spaces of the cartridges 101, 102 are limited, on their rear sides (on the top in FIG. 13, and on the bottom right in FIG. 14), by a first dispensing plunger 105 in the first cartridge 101 and a second dispensing plunger 106 in the second cartridge 102, whereby the dispensing plungers 105, 106 close off the internal spaces of the cartridges 101, 102 towards the outside in fluid-proof manner. Accordingly, the dispensing plunger 105 of the first cartridge 101 comprises a lateral recess such that it can glide over the second cartridge 102. Matching the smaller internal space, the dispensing plunger 106 of the second cartridge 102 has a smaller diameter than the dispensing plunger 105 of the first cartridge 101.

The internal space of the second cartridge 102 is shaped to be cylindrical with a circular footprint. The internal space of the first cartridge 101 is also shaped to be cylindrical with a circular footprint, whereby the second cartridge 102 takes up a part of the internal space of the first cartridge 101 and thus effects a discontinuation of the circular cylindrical symmetry of the internal space of the first cartridge 101. The dispensing plunger 105 of the first cartridge 101 comprises, on its rear side (on the top in FIG. 13, on the bottom in FIG. 14), a depression into which a pressing device 107 is plugged. The pressing device 107 comprises, on its rear side, a clamping edge 108 that engages the space in the internal space of the first cartridge 101 that is occupied by the second cartridge 102, when the pressing device 107 is being propelled forward (towards the top left in FIGS. 14, 16 and 17, towards the bottom right in FIG. 13) within the first cartridge 101. The clamping edge 108 comprises a chamfered surface that is inclined in the direction perpendicular to the cylinder axis of the second cartridge 102. The second cartridge 102 has a volume that corresponds to about one-twentieth [of the volume] of the first cartridge 101. Accordingly, the cement dough is mixed from the two starting components at a mixing ratio of approximately 20 to 1. Due to the cylindrical symmetry of the internal spaces of the cartridges 101, 102, the mixing ratio remains constant during the extrusion process.

The clamping edge 108 or the entire pressing device 107 consist of and/or are appropriately shaped from a material such that the pressing device 107 or at least the clamping edge 108 is harder or more solid than the wall of the second cartridge 102. Preferably, the clamping edge 108 and the entire pressing device 107 consist of a metal, in particular an aluminium alloy, or a solid plastic material that is at least harder, more solid and/or tougher than the material of the wall of the second internal cartridge 102, for example a fibre-reinforced plastic material.

The dispensing plungers 105, 106 are axially supported as in bearings such as to be mobile in longitudinal direction in the internal space of the cartridges 101, 102 in the direction of a cartridge head 109 of the cartridges 101, 102 (towards the left top, away from the observer, in FIGS. 14, 16, and 17, and towards the right bottom, towards the observer, in FIG. 13). An opening 22 of the first cartridge 101 and an opening of the second cartridge 102 are provided in the cartridge head 109. In the storage state of the storage and mixing system (see FIG. 13), a union nut 110 is screwed on in the region of the cartridge head 109 and is used to hold a rubber-elastic plate 141 that limits the two openings and forms a part of the cartridge head 109. Two stoppers 112, 114 are plugged into the openings and close the openings and thus close the internal spaces of the cartridges 101, 102 on the front side in fluid-proof manner.

An external thread 116 is provided on the outside of the front side of the first cartridge 101 as attachment element 116, onto which the union nut 110 can be screwed. For this purpose, the union nut 110 comprises a matching internal thread 118 as a counter-attachment element 118. A socket with a connector 120 for attachment of an extrusion device (not shown) is provided on the rear side of the storage and mixing system. The extrusion device supports the external first cartridge 101 and comprises a pestle by means of which the pressing device 107 can be pushed in the direction of the cartridge head 109. Preferably, the extrusion device is driven manually.

Analogous to the first exemplary embodiment, the dispensing tube 26 can be attached to the front side of the first cartridge 101 and is designed analogous to the first exemplary embodiment according to FIGS. 1 to 5. To attach the dispensing tube 26 to the first cartridge 101, the union nut 110 is unscrewed and the stoppers 112, 114 are removed and the cartridges 101, 102 are thus opened. Subsequently, the dispensing tube 26 is screwed onto the external thread 116. The dispensing tube 26 can be part of the storage and mixing system according to the invention.

When the dispensing tube 26 is attached to the first cartridge 101, the storage and mixing system is inserted into the extrusion device (not shown) and is connected to the extrusion device by means of the connector 120. The pestle of the extrusion device is driven into the storage and mixing system on the bottom side and thus presses onto the pressing device 107 on the bottom side. Since the first dispensing plunger 105 is connected to the pressing device 107, it is inserted into the first cartridge 101 by the pressing device 107 and, in the process, the first component 103 is pushed from the first cartridge 101 into the dispensing tube 26. Simultaneously, the wall of the second cartridge 102 is pushed in the direction of the internal wall of the first cartridge 101 by the clamping edge 108. Due to the deformation of the wall of the second cartridge 102, the second dispensing plunger 106 is being pushed in the direction of the cartridge head 109 and thus the second starting component 104 in the interior of the second cartridge 102 is pressed into the dispensing tube 26.

Since the wall of the second cartridge 102 is compressed by the second dispensing plunger 106 only after the second starting component 104 is expelled and/or is compressed behind the second dispensing plunger 106, the creases that are generated when the wall of the second cartridge 102 is being compressed do not retain residual amounts of the second starting component 104 and thus the mixing ratio in the cement dough is not being falsified.

Using the inventive design of the storage and mixing system, even very small amounts of the second starting component 104 can be admixed at the correct and/or desired mixing ratio. Conventional extrusion devices with a central pestle can be used for mixing and dispensing the cement dough, since the wall of the second cartridge 102 is being pushed outwards in the direction of the first cartridge 101 and thus is not in the way of the motion of the pestle.

The external first cartridge 101 can be designed to be appropriately narrow, preferable, according to the invention, with an internal diameter of maximally 25 mm or particularly preferably with an internal diameter of maximally 20 mm, such that the viscous starting components 103, 104, in particular the viscous first starting component 103, can be pushed into the dispensing tube 26 and through the static mixers 34 in the dispensing tube 26 without the resistance of the viscous pastes 103, 104 being so large that these can no longer be expelled with conventional, manually driven extrusion devices.

The features of the invention disclosed in the preceding description and in the claims, figures, and exemplary embodiments, can be essential for the implementation of the various embodiments of the invention both alone and in any combination.

LIST OF REFERENCE NUMBERS 1, 51, 101 External first cartridge
2, 52, 102 Internal second cartridge
3, 53 First starting component
4, 54 Second starting component
5, 55, 105 First dispensing plunger
6, 56, 106 Second dispensing plunger
7, 57, 107 Pressing device
8, 58, 108 Clamping edge
9, 59, 109 Cartridge head
10, 60, 110 Union nut
12, 62, 112 Stopper
14, 64, 114 Stopper
16, 66, 116 External thread/attachment element
18, 68, 118 Internal thread/attachment element
20, 70, 120 Connector
22, 72 Opening of the first cartridge
24, 74 Opening of the second cartridge
26, 74 Dispensing tube
28 Internal thread
30 Socket
32 Seal
34 Static mixer
36 Dispensing opening
38, 75, 138 Snap-in means/depression
40 Seal/elevation
41, 71, 141 Rubber-elastic plate
42, 77 Seal/elevation
61 Internal third cartridge
63 Third starting component
65 Stopper
67 Third dispensing plunger
73 Opening of the third cartridge
78 Seal/elevation
80, 90 Pressing device
82, 92 Clamping edge
84, 94 Pressing surface for pestle
86, 96 Fin

We claim:

1. A storage and mixing system for pasty multicomponent polymethylmethacrylate bone cements, the storage and mixing system comprising
a first tubular cartridge with a first internal space, whereby a first starting component of a multicomponent bone cement is contained in the first internal space;
a first dispensing plunger that is arranged in the first internal space of the first cartridge such as to be axially mobile and that is provided for expelling the first starting component from the first cartridge through an opening in a cartridge head of the first cartridge that is opposite from the first dispensing plunger;

a second tubular cartridge that is arranged within the first tubular cartridge, whereby an external wall of the second cartridge touches against an internal wall of the first cartridge and is attached to the internal wall of the first cartridge, whereby the second cartridge contains a second starting component of the multicomponent bone cement and has a second dispensing plunger arranged therein, whereby the second dispensing plunger is movable to expel the second starting component from the second cartridge through an opposite opening in the second cartridge in a region of the cartridge head of the first cartridge; and a pressing device arranged with a clamping edge for compressing the second cartridge that can be propelled axially in the first internal space of the first cartridge, as seen from the cartridge head, behind the first dispensing plunger and the second dispensing plunger, wherein the pressing device is propellable appropriately in a direction of the cartridge head such that the second cartridge is being progressively compressed axially during the motion of the pressing device such that, in the process, the first dispensing plunger and the second dispensing plunger are propelled in the direction of the cartridge head, wherein the camping edge, by squeezing the second cartridge, presses a deformed wall of the second cartridge against an underside of the second dispensing plunger and thus pushes the second dispensing plunger in the direction of the cartridge head while the pressing device is being propelled in the direction of the cartridge head.

2. The system according to claim 1, wherein the external wall of the second cartridge is attached to the internal wall of the first cartridge, in a front in an area of the cartridge head and in a back behind the second dispensing plunger.

3. The system according to claim 2, wherein a third tubular cartridge is arranged within the first tubular cartridge, wherein the external wall of the third cartridge touches against the internal wall of the first cartridge and is attached to the internal wall of the first cartridge, wherein the third cartridge contains the second starting component or a third starting component of the multicomponent bone cement and has a third dispensing plunger arranged in it, wherein the third dispensing plunger can be used to expel the second starting component for the third starting component from the third cartridge through an opposite opening in the third cartridge in the region of the cartridge head of the first cartridge, wherein the pressing device is arranged, as seen from the cartridge head, behind the third dispensing plunger and the pressing device comprises a clamping edge for compressing the third cartridge, whereby the pressing device can be propelled can be propelled appropriately in the direction of the cartridge head such that the third cartridge is being progressively compressed axially during the motion of the pressing device such that, in the process, the first dispensing plunger, the second dispensing plunger, and the third dispensing plunger are propelled in the direction of the cartridge head.

4. The system according to claim 3, wherein the third cartridge and/or the third dispensing plunger have the same features as the second cartridge and/or the second dispensing plunger.

5. The system according to claim 4, wherein at least one fourth tubular cartridge is arranged inside the first tubular cartridge, wherein the external wall of the at least one fourth cartridge touches against the internal wall of the first cartridge and is attached to the internal wall of the first cartridge, whereby the at least one fourth cartridge contains the second, the third, a fourth and/or each at least one further starting component of the bone cement and the at least one fourth cartridge has a fourth dispensing plunger each arranged in it, whereby the second, the third, the fourth and/or the respective further starting component can be expelled from the at least one fourth cartridge, by means of the fourth dispensing plunger, through an opposite opening in the at least one fourth cartridge in the region of the cartridge head of the first cartridge, wherein the pressing device is arranged behind the fourth dispensing plunger or plungers, as seen from the cartridge head and the pressing device comprises at least one clamping edge for compressing the at least one fourth cartridge, whereby the pressing device can be propelled appropriately in the direction of the cartridge head such that the at least one fourth cartridge is progressively compressed axially while the pressing device moves and thus the first dispensing plunger, the second dispensing plunger, the third dispensing plunger, and the fourth dispensing plunger or plungers are being propelled in the direction of the cartridge head.

6. The system according to claim 2, wherein the external wall of the second cartridge is attached to the internal wall of the first cartridge along an entire length of the second cartridge.

7. The system according to claim 1, wherein an opening and an opposite opening openings are closeable on the cartridge head by means of a detachable closure.

8. The system according to claim 1, wherein the first dispensing plunger and the second dispensing plunger are propelled parallel with respect to each other during the propulsion of the pressing device.

9. The system according to claim 8, wherein the first dispensing plunger and the second dispensing plunger run at a same level in the direction of the cartridge head.

10. The system according to claim 1, wherein an external thread is provided on an outside of the first cartridge in the region of the cartridge head.

11. The system according to claim 1, further comprising a dispensing tube with a static mixer that is attachable to the first cartridge.

12. The system according to claim 11, wherein a ratio of the internal diameter of the first cartridge and the internal diameter of the dispensing tube is less than 5 to 2.

13. The system according to claim 1, wherein the clamping edge is inclined at an angle of at least 40° with respect to a longitudinal axis of the first cartridge.

14. The system according to claim 1, wherein the clamping edge squeezes the second cartridge against the internal wall of the first cartridge when the pressing device is being propelled.

15. The system according to claim 1, wherein the clamping edge covers at least 30% of a surface area of a cross-section of the second cartridge.

16. The system according to claim 1, wherein a gap is provided between the pressing device and the internal wall of the first cartridge in a region of the second cartridge, wherein the gap is as wide as or wider than a thickness of the wall of the second cartridge.

17. The system according to claim 1, wherein a rear side of the pressing device is designed as a support surface for a pestle of an extrusion device.

18. The system according to claim 1, wherein a diameter of the internal space of the first cartridge is smaller than or equal to 25 mm.

19. The system according to claim 1, wherein the first cartridge, the second cartridge, the cartridge head, and the dispensing plungers are made from plastic material.

20. The system according to claim 19, wherein the plastic material is selected from the group consisting polyethylene-co-vinylalcohol, polybutylene-terephthalate, polyethylene-terephthalate, and polymethacryl acid methylester-co-acrylonitrile.

21. The system according to claim 1, wherein the ratio of the volume of the first cartridge and the volume of the second cartridge is at least 95 to 5.

22. The system according to claim 1, wherein the second cartridge is squeezed appropriately, when the pressing device is exposed to at least 0.5 kN acting in the direction of the cartridge head, such that the squeezed second cartridge fits through a gap between the clamping edge and the internal wall of the first cartridge.

23. The system according to claim 1, wherein the ratio of the thickness of the wall of the first cartridge and the thickness of the wall of the second cartridge is at least 11 to 10.

24. The system according to claim 1, wherein over the entire length of the second cartridge or over at least 80% of the entire length of the second cartridge, and/or a part of the wall of the first cartridge limits a part of a second internal space of the second cartridge.

25. A method for the mixing of the starting components of a pasty cement dough using the storage and mixing system according to claim 1, the method comprising in the given order,
   a) removing the cartridge head from the first cartridge or opening the openings of the first cartridge and of the second cartridge;
   b) attaching and connecting a dispensing tube to the front side of the first cartridge;
   c) inserting the first cartridge into an extrusion device, whereby the extrusion device comprises a pestle that can be propelled axially for propelling the pressing device on the interior of the first cartridge in the direction of the dispensing tube; and
   d) extruding the starting components by means of the extrusion device by axially propelling the pestle, whereby the pressing device is propelled in the direction of the dispensing tube by the pestle, the first dispensing plunger is pushed in the direction of the dispensing tube by the pressing device, the clamping edge of the pressing device presses the wall of the second cartridge to the internal wall of the first cartridge, the deformed wall of the second cartridge pushes the second dispensing plunger in the second cartridge in the direction of the dispensing tube, whereby the starting components of the cement dough of both cartridges are being pushed into the dispensing tube, whereby the starting components are mixed in the dispensing tube to form the pasty cement dough and the mixed cement dough flows out from a dispensing opening of the dispensing tube.

26. The method according to claim 25, wherein the third cartridge is opened in a) and at least one fourth cartridge are openable and, during propulsion of the pressing device with the pestle in the direction of the dispensing tube in step d), the clamping edge of the pressing device presses the wall of the third cartridge to the internal wall of the first cartridge, the deformed wall of the third cartridge pushes the third dispensing plunger in the third cartridge in the direction of the dispensing tube.

27. The method according to claim 25, wherein the extrusion device is driven manually, by compressed air or by a motor, whereby the manual force, the compressed air or the motor propels the pestle in the direction of the dispensing tube.

* * * * *